United States Patent
Hishida et al.

(10) Patent No.: US 10,068,349 B2
(45) Date of Patent: Sep. 4, 2018

(54) IMAGE ANALYSIS APPARATUS, IMAGE ANALYSIS METHOD, AND PROGRAM

(71) Applicants: IHI CORPORATION, Koto-ku (JP); THE UNIVERSITY OF TOKYO, Bunkyo-ku (JP)

(72) Inventors: Hiroyuki Hishida, Koto-ku (JP); Koichi Inagaki, Koto-ku (JP); Takeshi Nakamura, Koto-ku (JP); Yu Hasegawa, Bunkyo-ku (JP); Hiromasa Suzuki, Bunkyo-ku (JP); Takashi Michikawa, Bunkyo-ku (JP); Yutaka Ohtake, Bunkyo-ku (JP); Suguru Kondo, Bunkyo-ku (JP)

(73) Assignees: IHI CORPORATION, Koto-ku (JP); THE UNIVERSITY OF TOKYO, Bunkyo-ku (JP)

(*) Notice: Subject to any disclaimer, the term of this patent is extended or adjusted under 35 U.S.C. 154(b) by 0 days.

(21) Appl. No.: 15/514,712

(22) PCT Filed: Sep. 29, 2015

(86) PCT No.: PCT/JP2015/077472
§ 371 (c)(1),
(2) Date: Mar. 27, 2017

(87) PCT Pub. No.: WO2016/052489
PCT Pub. Date: Apr. 7, 2016

(65) Prior Publication Data
US 2017/0213357 A1     Jul. 27, 2017

(30) Foreign Application Priority Data
Sep. 29, 2014    (JP) ................................ 2014-199406

(51) Int. Cl.
*G06T 7/60*       (2017.01)
*D06H 3/08*      (2006.01)
(Continued)

(52) U.S. Cl.
CPC ................. *G06T 7/60* (2013.01); *D06H 3/08* (2013.01); *G01N 21/8851* (2013.01);
(Continued)

(58) Field of Classification Search
CPC . G06T 2207/10081; G06T 2207/10028; G06T 2207/30101; G06T 2207/30164;
(Continued)

(56) References Cited

U.S. PATENT DOCUMENTS 6,526,305 B1* 2/2003 Mori ................ G01R 33/56341
                                                            128/920
7,027,651 B2* 4/2006 Simon .................. G06K 9/6205
                                                            382/209

(Continued)

FOREIGN PATENT DOCUMENTS

JP         2012-2547 A     1/2012
WO     2015/046534 A1    4/2015

OTHER PUBLICATIONS

"Woven Fabric Model Creation from a Single Image."; Guarnera, Giuseppe Claudio; Hall, Peter; Chesnais, Alain; Glencross, Mashhuda; ACM Transactions on Graphics; Oct. 2017, vol. 36 Issue 5, p. 1-13, 13p.*

(Continued)

*Primary Examiner* — Michael Osinski
(74) *Attorney, Agent, or Firm* — Oblon, McClelland, Maier & Neustadt, L.L.P.

(57) ABSTRACT

An image analysis apparatus, which analyzes orientations of fiber bundles of X-yarns and Y-yarns from a three-dimensional image of a woven fabric made of fiber bundles of the (Continued)

X-yarns, the Y-yarns, and Z-yarns, includes: a binarization unit that binarizes the three-dimensional image; an overlapping area extraction unit that extracts an overlapping area from the binarized image; a reference direction determination unit that averages an overlapping direction of each voxel included in the overlapping area and determines the averaged direction as a reference direction; a Z-yarn removal unit that removes the Z-yarns from the binarized image by applying a directional distance method on a reference plane perpendicular to the reference direction; and a fiber bundle orientation estimation unit that applies the directional distance method on the reference plane and estimates the orientations of the fiber bundles of the X-yarns and the Y-yarns based on a calculated directional distance.

16 Claims, 29 Drawing Sheets

(51) Int. Cl.
  G01N 23/04 (2018.01)
  G06T 7/00 (2017.01)
  G01N 21/88 (2006.01)
  G01N 21/84 (2006.01)
  G06T 7/73 (2017.01)

(52) U.S. Cl.
  CPC ............ G01N 23/04 (2013.01); G06T 7/00 (2013.01); G06T 7/73 (2017.01); G01N 2021/8444 (2013.01); G01N 2021/8887 (2013.01); G06T 2207/30124 (2013.01)

(58) Field of Classification Search
  CPC . G06T 2207/30124; G06T 2207/20036; G06T 2200/04; G06T 7/0004; G06T 7/11; G06T 7/12; G06T 7/60; G06T 7/155; G06T 7/70; G06T 7/73; G06T 7/74; G06T 7/75; G01N 23/046; G01N 2021/8887; G06K 9/00201; G06K 9/4604; G06K 9/6215; G06K 9/00523; G06K 9/00536; G06K 9/627

See application file for complete search history.

(56) References Cited

U.S. PATENT DOCUMENTS

| | | | | |
|---|---|---|---|---|
| 7,127,107 B2* | 10/2006 | Kubota | G06T 7/12 | 382/199 |
| 7,639,253 B2* | 12/2009 | Bae | G06T 17/00 | 345/419 |
| 7,822,254 B2* | 10/2010 | Yatziv | G06T 7/30 | 345/419 |
| 7,949,162 B2* | 5/2011 | Odry | G06T 7/0012 | 382/128 |
| 7,970,189 B2* | 6/2011 | Buelow | G06T 7/155 | 382/128 |
| 8,699,786 B2* | 4/2014 | Kotake | G06T 7/55 | 382/154 |
| 8,854,430 B2* | 10/2014 | Varslot | G06T 7/30 | 348/46 |
| 8,885,926 B2* | 11/2014 | Seung | G06T 7/0081 | 382/128 |
| 9,412,019 B2* | 8/2016 | Chen | G06K 9/00201 | |
| 9,443,297 B2* | 9/2016 | Beaudoin | G06T 7/0004 | |
| 9,811,898 B2* | 11/2017 | Hishida | G06T 7/001 | |
| 9,824,435 B2* | 11/2017 | Hishida | G06T 7/0004 | |
| 2002/0181780 A1* | 12/2002 | Simon | G06K 9/6205 | 382/209 |
| 2003/0165258 A1* | 9/2003 | Kubota | G06T 7/12 | 382/113 |
| 2007/0116343 A1* | 5/2007 | Sauer | G06T 5/50 | 382/131 |
| 2007/0274582 A1* | 11/2007 | Yatziv | G06T 7/30 | 382/131 |
| 2008/0012851 A1* | 1/2008 | Bae | G06T 17/00 | 345/419 |
| 2008/0040083 A1* | 2/2008 | Odry | G06T 7/0012 | 703/2 |
| 2008/0122440 A1* | 5/2008 | Sakai | G01R 33/56341 | 324/309 |
| 2009/0034810 A1* | 2/2009 | Oakley | G06K 9/44 | 382/128 |
| 2009/0208095 A1* | 8/2009 | Zebedin | G06T 17/05 | 382/154 |
| 2010/0128940 A1* | 5/2010 | Buelow | G06T 7/11 | 382/128 |
| 2010/0135560 A1* | 6/2010 | Embleton | G01R 33/56341 | 382/131 |
| 2010/0266175 A1* | 10/2010 | Seung | G06T 7/0081 | 382/128 |
| 2011/0150279 A1* | 6/2011 | Kotake | G06K 9/4604 | 382/103 |
| 2011/0181701 A1* | 7/2011 | Varslot | G06T 7/0026 | 348/46 |
| 2011/0304619 A1* | 12/2011 | Fu | G06T 17/00 | 345/420 |
| 2013/0167374 A1* | 7/2013 | Kirby | C04B 35/64 | 29/888.02 |
| 2014/0185874 A1* | 7/2014 | Li | G06K 9/00201 | 382/103 |
| 2014/0185923 A1* | 7/2014 | Chen | G06K 9/00201 | 382/154 |
| 2014/0198979 A1* | 7/2014 | Hamarneh | A61B 6/03 | 382/154 |
| 2014/0370282 A1* | 12/2014 | Yamamoto | H01G 11/86 | 428/367 |
| 2015/0015602 A1* | 1/2015 | Beaudoin | G06T 7/0004 | 345/619 |
| 2015/0254850 A1* | 9/2015 | Jorgensen | G06T 7/0016 | 382/133 |
| 2016/0232653 A1* | 8/2016 | Hishida | G01N 23/04 | |
| 2016/0247271 A1* | 8/2016 | Hishida | G01N 23/04 | |

OTHER PUBLICATIONS

T. Shinohara, et al., "Extraction of Yarn Positional Information from a Three-dimensional CT Image of Textile Fabric using Yarn Tracing with a Filament Model for Structure Analysis," Textile Research Journal, vol. 80, No. 7, 2010, pp. 623-630.
Y. Yamauchi, et al., "Extracting Woven Yarns of Ceramic Matrix Composite Parts with X-ray CT Scanning," iCT Conference 2014, 7 pages.
Y. Hasegawa, et al., "A Study on Inner Defects Detection of CMC Material by Using CT Image," 2014, 6 pages (with partial English translation).
Y. Yamauchi, et al., "A Basic Research for Recognition of Fibrous Structure by CT Volume Image," 2012, 8 pages (with partial English translation).
International Search Report dated Dec. 15, 2015 in PCT/JP2015/077472 filed Sep. 29, 2015.
Canadian Office Action issued in Canadian Patent Application No. 2,961,455 dated Feb. 26, 2018.
Wirjadi et al., "Applications of Anisotropic Image Filters for Computing 2D and 3D-Fiber Orientations," Proceedings of the 10$^{th}$ European Conference in Image Analysis and Stereology, ECS10, pp. 1-6, XP055359380, (Jun. 29, 2009).
Bale et al., "Characterizing Three-Dimensional Textile Ceramic Composites Using Synchrotron X-Ray Micro-Computed-Tomography," Journal of the American Ceramic Society, vol. 95, No. 1, pp. 392-402, XP055331937, (Jan. 31. 2012).
European Search Report issued in European Application No. 15 84 6683 dated May 8, 2018, citing references AW and AX therein.

* cited by examiner

IMAGE ANALYSIS APPARATUS, IMAGE ANALYSIS METHOD, AND PROGRAM

TECHNICAL FIELD

Embodiments described herein relate to an image analysis apparatus, an image analysis method, and a program. Particularly, the disclosure is suited for use in an image analysis apparatus, image analysis method, and program for analyzing orientations of fiber bundles included in a fiber-reinforced composite material.

BACKGROUND ART

In recent years, the development of Ceramic Matrix Composites (CMC), a type of fiber-reinforced composite materials, has been being promoted. The CMC is a composite material which is ceramic fibers reinforced with a base material (matrix) and is characterized by light weight and excellent heat resistance. The use of the CMC as, for example, aircraft engine components by utilizing these characteristics is being examined and its practical use is currently being promoted. A significant improvement in fuel efficiency can be expected by using the CMC as the aircraft engine components.

A general forming process of the CMC is described as follows. Firstly, about several hundreds of ceramic fibers are tied together to make fiber bundles and these fiber bundles are woven to manufacture a woven fabric. Methods for weaving the fiber bundles include, for example, three-dimensional weaving or plain weaving. The three-dimensional weaving is a method for manufacturing the woven fabric by weaving the fiber bundles in three directions, that is, XYZ-directions and the plain weaving is a method for manufacturing the woven fabric by weaving the fiber bundles in two directions, that is, XY-directions.

After the woven fabric is manufactured, matrixes are formed by means of CVI (Chemical Vapor Infiltration) and PIP (Polymer Impregnation and Pyrolysis); and lastly, machining, surface coating, and so on are performed, thereby forming the CMC. Under this circumstance, orientations of the fiber bundles of the then-formed CMC significantly influence the strength of the CMC.

Specifically speaking, when the fiber bundles wind at places where they should be straight, or when the fiber bundles generally deviate from their reference axis where they should originally be located, or when the fiber bundles break in the middle of the CMC forming process, the strength of the CMC degrades. On the other hand, when the fiber bundles are properly arranged in certain directions without winding, deviating, or breaking, high strength and excellent heat resistance are achieved. Therefore, orientations of the fiber bundles are evaluated in order to check if the strength of the formed CMC is sufficient or not.

PTL 1 discloses an orientation analysis method for acquiring a binary image by binarizing a slice image of a resin molded product, acquiring a power spectrum image by performing Fourier transformation of this binary image, and determining a main axial direction of an ellipse perpendicular to an ellipse drawn by this power spectrum image to be an orientation direction of a filler (fibers) contained in the resin molded product.

Furthermore, NPL 1 discloses a technique that acquires an X-ray CT image of a woven fabric, in which fiber bundles are woven, by capturing the image using an X-ray CT scanner and performs calculation by using a special filter function on this X-ray CT image, thereby analyzing the orientation of each one of fibers constituting the fiber bundles.

CITATION LIST

Patent Literature

PTL 1: Japanese Patent Application Laid-Open (Kokai) Publication No. 2012-2547

Non-Patent Literature

NPL 1: T. Shinohara, J. Takayama, S. Ohyama, and A. Kobayashi, "Extraction of Yarn Positional Information from a Three-dimensional CT Image of Textile Fabric using Yarn Tracing with a Filament Model for Structure Analysis", Textile Research Journal, Vol. 80, No. 7, pp. 623-630 (2010)

SUMMARY

Problems to be Solved

However, the technique of PTL 1 can obtain only one direction as the analysis result with respect to the orientation of the filler (fibers) contained in the slice image. Therefore, when the fiber bundles are arranged in a plurality of directions as in, for example, the three-dimensional weaving or the plain weaving, the orientations of the respective fiber bundles cannot be obtained as the analysis results. It is also impossible to analyze whether or not the fiber bundles are properly arranged and aligned in certain directions without winding, deviating, or breaking.

Moreover, regarding the technique described in NPL 1, a high-definition X-ray CT image in which each one of the fibers constituting the fiber bundles can be identified is obtained. In this case, imaging time to obtain the X-ray CT image becomes long, so that this technique cannot be used for product testing and, therefore, is not practical. Furthermore, this technique is effective for fibers which have a circular cross section; however, this technique cannot be used directly as a technique to analyze orientations of fiber bundles which have a fattened cross section. Furthermore, a starting point of each fiber in the X-ray CT image is input, which results in a problem of troublesome operations.

The present disclosure is disclosed in consideration of the above-described circumstances and proposes an image analysis apparatus, image analysis method, and program capable of easily analyzing the orientations of fiber bundles from a three-dimensional image of the CMC.

Means to Solve the Problems

In order to solve the above-described problems, provided according to the disclosure of the present disclosure is an image analysis apparatus for analyzing orientations of fiber bundles of X-yarns and Y-yarns from a three-dimensional image of a woven fabric made of fiber bundles of the X-yarns, the Y-yarns, and Z-yarns, wherein the image analysis apparatus includes: a binarization unit that binarizes the three-dimensional image; an overlapping area extraction unit that extracts an overlapping area, in which the X-yarns and the Y-yarns perpendicularly and three-dimensionally intersect with each other, from the binarized image; a reference direction determination unit that averages an overlapping direction of each voxel included in the overlapping area and determines the averaged direction as a reference direction; a Z-yarn removal unit that removes the Z-yarns from the binarized image by applying a directional distance method on a reference plane perpendicular to the reference direction; and a fiber bundle orientation estimation unit that applies the directional distance method again to the image, from which the Z-yarns have been removed, on the reference plane and estimates the orientations of the fiber bundles of the X-yarns and the Y-yarns on the basis of a directional distance calculated upon the application.

Furthermore, in order to solve the above-described problems, provided according to the disclosure of the present disclosure is an image analysis method for analyzing orientations of fiber bundles of X-yarns and Y-yarns from a three-dimensional image of a woven fabric made of fiber bundles of the X-yarns, the Y-yarns, and Z-yarns, wherein the image analysis method includes the following steps executed by a computer: a first step of binarizing the three-dimensional image; a second step of extracting an overlapping area, in which the X-yarns and the Y-yarns perpendicularly and three-dimensionally intersect with each other, from the binarized image; a third step of averaging an overlapping direction of each voxel included in the overlapping area and determining the averaged direction as a reference direction; a fourth step of removing the Z-yarns from the binarized image by applying a directional distance method on a reference plane perpendicular to the reference direction; and a fifth step of applying the directional distance method again to the image, from which the Z-yarns have been removed, on the reference plane and estimating the orientations of the fiber bundles of the X-yarns and the Y-yarns on the basis of a directional distance calculated upon the application.

Furthermore, in order to solve the above-described problems, provided according to the disclosure of the present disclosure is a program for analyzing orientations of fiber bundles of X-yarns and Y-yarns from a three-dimensional image of a woven fabric made of fiber bundles of the X-yarns, the Y-yarns, and Z-yarns, wherein the program causes a computer to execute: a first step of binarizing the three-dimensional image; a second step of extracting an overlapping area, in which the X-yarns and the Y-yarns perpendicularly and three-dimensionally intersect with each other, from the binarized image; a third step of averaging an overlapping direction of each voxel included in the overlapping area and determining the averaged direction as a reference direction; a fourth step of removing the Z-yarns from the binarized image by applying a directional distance method on a reference plane perpendicular to the reference direction; and a fifth step of applying the directional distance method again to the image, from which the Z-yarns have been removed, on the reference plane and estimating the orientations of the fiber bundles of the X-yarns and the Y-yarns on the basis of a directional distance calculated upon the application.

Furthermore, in order to solve the above-described problems, an image analysis apparatus of the present disclosure includes: a binarization unit that binarizes a three-dimensional image of a woven fabric made of fiber bundles of X-yarns, Y-yarns, and Z-yarns; an overlapping area extraction unit that extracts an overlapping area, in which the X-yarns and the Y-yarns perpendicularly and three-dimensionally intersect with each other, from the binarized image; and an overlapping area morphological analysis unit that analyzes a form of the extracted overlapping area.

Furthermore, in order to solve the above-described problems, an image analysis method of the present disclosure includes: a step of binarizing a three-dimensional image of a woven fabric made of fiber bundles of X-yarns, Y-yarns, and Z-yarns; a step of extracting an overlapping area, in which the X-yarns and the Y-yarns perpendicularly and three-dimensionally intersect with each other, from the binarized image; and a step of analyzing a form of the extracted overlapping area.

Furthermore, in order to solve the above-described problems, a program of the present disclosure causes a computer to execute: a step of binarizing a three-dimensional image of a woven fabric made of fiber bundles of X-yarns, Y-yarns, and Z-yarns; a step of extracting an overlapping area, in which the X-yarns and the Y-yarns perpendicularly and three-dimensionally intersect with each other, from the binarized image; and a step of analyzing a form of the extracted overlapping area.

Effects

According to the disclosure of the present disclosure, the orientations of fiber bundles can be easily analyzed from a three-dimensional image of the CMC.

DESCRIPTION OF EMBODIMENTS

An embodiment of the present disclosure will be explained in detail with reference to drawings.

(1) Overall Configuration of Image Analysis Apparatus 1

Figure 1:
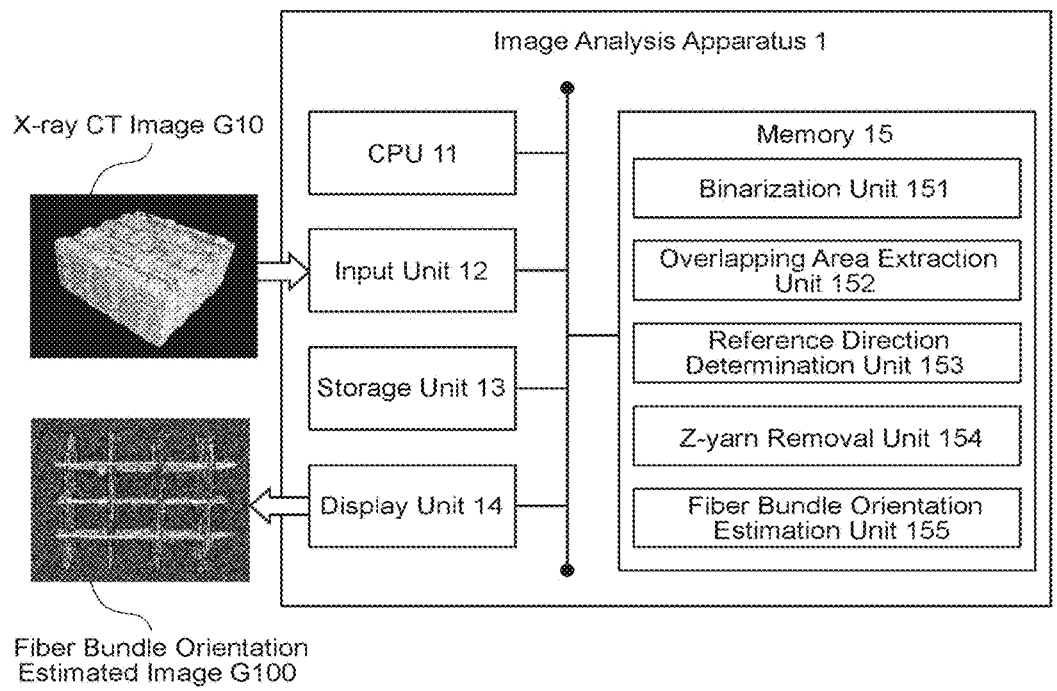
FIG. 1 is an overall configuration diagram of an image analysis apparatus.

FIG. 1 illustrates an overall configuration of an image analysis apparatus 1 according to this embodiment. The image analysis apparatus 1 is a computer configured by including a CPU (Central Processing Unit) 11, an input unit 12, a storage unit 13, a display unit 14, and a memory 15.

The CPU 11 is a processor for controlling the operation of the image analysis apparatus 1 in a supervisory manner in cooperation with various programs stored in the memory 15. The input unit 12 is an interface for accepting inputs from a user and is, for example, a keyboard and a mouse. The input unit 12 according to this embodiment is also an interface for inputting an X-ray CT image G10 of a woven fabric which constitutes a CMC (Ceramic Matrix Composite).

The CMC herein used is a fiber-reinforced composite material formed by making fiber bundles by tying about several hundreds of ceramic fibers together, manufacturing a woven fabric by weaving these fiber bundles, then coating the surfaces of the fibers with carbons or the like, and then performing, for example, a CVI (Chemical Vapor Infiltration) process and a PIP (Polymer Impregnation and Pyrolysis) process to form matrixes.

Weaving methods for manufacturing a woven fabric include those called three-dimensional weaving or plain weaving. The three-dimensional weaving is a method for manufacturing the woven fabric by weaving the fiber bundles in three directions, that is, XYZ-directions and the plain weaving is a method for manufacturing the woven fabric by weaving the fiber bundles in two directions, that is, XY-directions.

Figure 2:
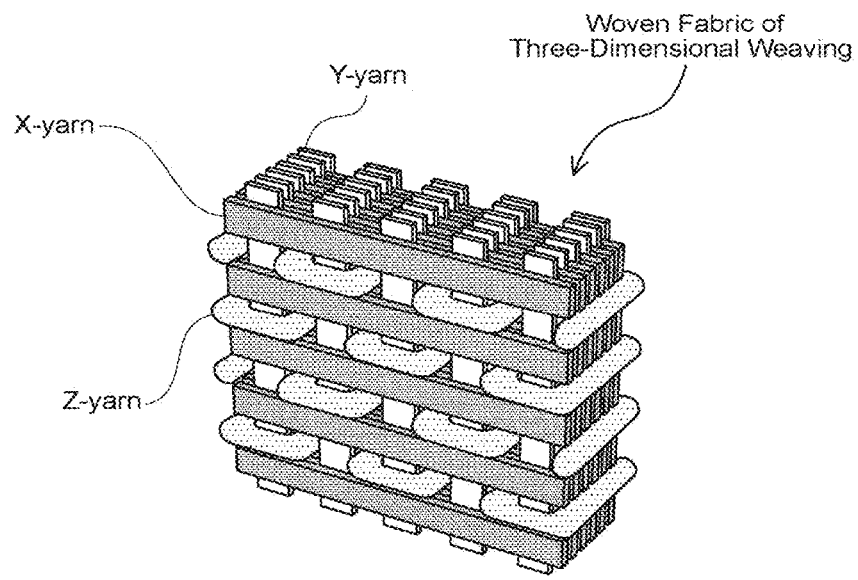
FIG. 2 is a conceptual diagram of a woven fabric of three-dimensional weaving.

FIG. 2 illustrates a conceptual diagram of a woven fabric of three-dimensional weaving. In this embodiment, an image of the woven fabric manufactured by particularly complicated three-dimensional weaving or an image of a CMC formed from this woven fabric is captured by using an X-ray CT scanner and an attempt is made to automatically analyze orientations of fiber bundles from the obtained X-ray CT image G10.

The woven fabric of three-dimensional weaving is formed as illustrated in FIG. 2 by alternately placing fiber layers, which are made of fiber bundles of X-yarns arranged at equal distances, and fiber layers, which are made of fiber bundles of Y-yarns arranged at equal distances, one on top of another and fixing the multiplicity of accumulated fiber layers with fiber bundles of Z-yarns so as to prevent the fiber layers from falling off during the CMC forming process.

The CMC which is formed from this woven fabric is designed by assuming that it expands and contracts normally in the X-yarn direction or the Y-yarn direction. Therefore, the Z-yarns which are interlaced substantially perpendicularly with the X-yarns and the Y-yarns do not directly influence the strength of the CMC. On the other hand, the existence of the Z-yarns may cause poor accuracy when analyzing the orientations of the X-yarns and the Y-yarns.

So, this embodiment is designed to remove the Z-yarns from the X-ray CT image G10 of the woven fabric of three-dimensional weaving and analyze the orientations of the fiber bundles of the X-yarns and the Y-yarns with good accuracy.

Incidentally, the orientation(s) is a term that generally means arrangement aligned, or a state of being arranged, in a certain direction(s) and is used with the same meaning in this embodiment. Even if the fiber bundles are arranged in a state of winding, deviating, or breaking, the state of their arrangement will be called the "orientation(s)" as long as the fiber bundles are arranged in a state of being aligned in a certain direction(s).

Referring back to FIG. 1, the storage unit 13 is a storage medium that stores the X-ray CT image G10 which is input from the input unit 12, and processed images obtained by executing various processing on this X-ray CT image G10. The display unit 14 is a display device such as an LCD (Liquid Crystal Display) that, for example, displays the X-ray CT image G10, images, and processed images. For example, the display unit 14 automatically analyzes the orientations of the fiber bundles from the X-ray CT image G10 and displays a fiber bundle orientation estimated image G100 on a display screen.

The memory 15 is a storage medium that stores various programs for executing image analysis processing in cooperation with the CPU 11. The various programs include a binarization unit 151, an overlapping area extraction unit 152, a reference direction determination unit 153, a Z-yarn removal unit 154, and a fiber bundle orientation estimation unit 155. The image analysis processing (FIG. 3) executed by these various programs will be explained later.

(2) Flowchart of Image Analysis Processing

Figure 3:
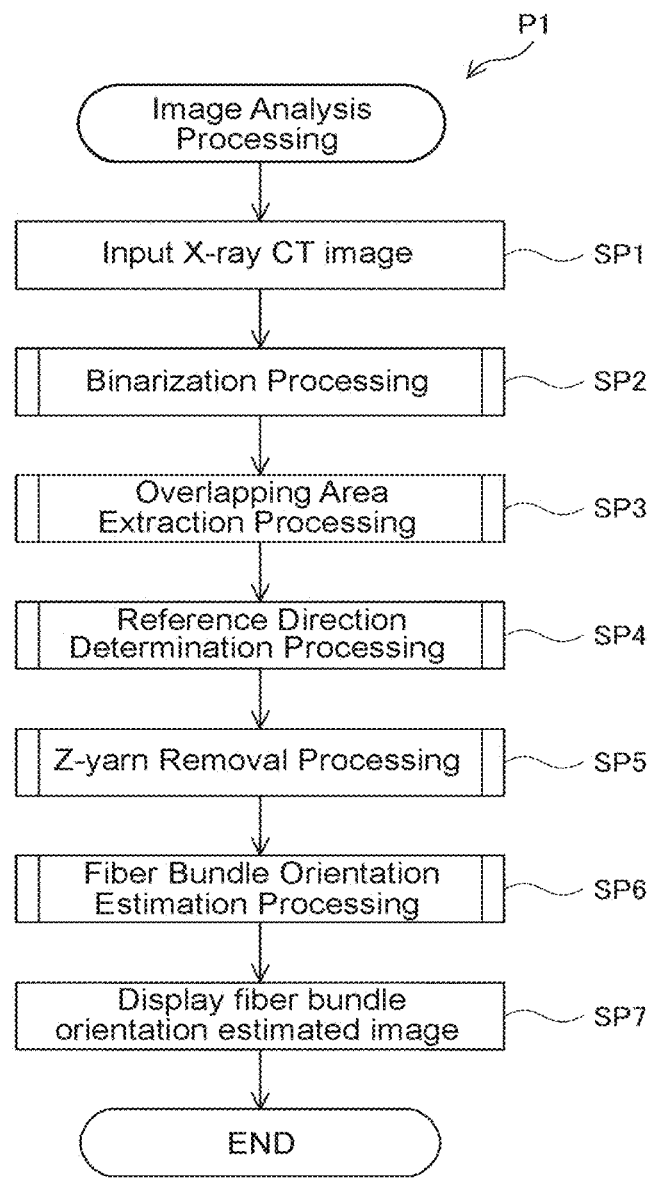
FIG. 3 is an entire flowchart of image analysis processing.

FIG. 3 illustrates an entire flowchart of image analysis processing P1 according to this embodiment. This image analysis processing is executed in cooperation between the CPU 11 and the various programs stored in the memory 15 as triggered by the reception of an execution instruction from the user by the input unit 12. For ease of explanation, the following explanation will be given by referring to the various programs as processing subjects.

After the binarization unit 151 firstly inputs the X-ray CT image G10 via the input unit 12 (SP1), it binarizes the input X-ray CT image G10 on the basis of a specified threshold value and creates a binary image in which respective fiber bundles of the X-yarns, the Y-yarns, and the Z-yarns are indicated on the foreground (SP2).

Then, the overlapping area extraction unit 152 extracts an overlapping area in which the X-yarns and the Y-yarns perpendicularly and three-dimensionally intersect with each other (SP3); and the reference direction determination unit 153 determines an overlapping direction of the extracted overlapping area as a reference direction (SP4).

The reason for extracting the overlapping area at this point is to estimate the overlapping direction by applying a normal directional distance method to the extracted overlapping area. The normal directional distance method will be explained later.

Furthermore, the reason for determining the overlapping direction as the reference direction is to estimate the orientations of the fiber bundles by applying the two-dimensional normal directional distance method on a plane perpendicular to this reference direction.

The plane perpendicular to the reference direction will be referred to as a "reference plane" and a method for applying the two-dimensional normal directional distance method on the reference plane will be referred to as a "referenced directional distance method."

Since the X-yarns or the Y-yarns exist on the reference plane, the orientations of the fiber bundles of the X-yarns and the Y-yarns can be estimated with good accuracy by applying the referenced directional distance method. The referenced directional distance method will be explained later.

Next, the Z-yarn removal unit 154 estimates the orientations of the fiber bundles of the X-yarns, the Y-yarns, and the Z-yarns by applying the referenced directional distance method to the binary image. Then, the Z-yarn removal unit 154 removes the Z-yarns included in the binary image on the basis of the estimated orientations (SP5).

Subsequently, the fiber bundle orientation estimation unit 155 estimates the orientations of the fiber bundles of the X-yarns and the Y-yarns by applying the referenced directional distance method again to the binary image from which the Z-yarns have been removed (SP6).

Then, the fiber bundle orientation estimation unit 155 creates the fiber bundle orientation estimated image G100, has the display unit 14 display the fiber bundle orientation estimated image G100 (SP7), and terminates this image analysis processing.

(3) Details of Each Processing

The details of each processing (SP2 to SP6) explained with reference to FIG. 3 will be explained below with reference to FIG. 4 to FIG. 17 and by using mathematical expressions (Expression 1 to Expression 3). Incidentally, since processing for inputting the X-ray CT image G10 (SP1) and processing for displaying the fiber bundle orientation estimated image G100 (SP7) are general methods, an explanation about them is omitted.

(3-1) Binarization Processing

Figure 4:
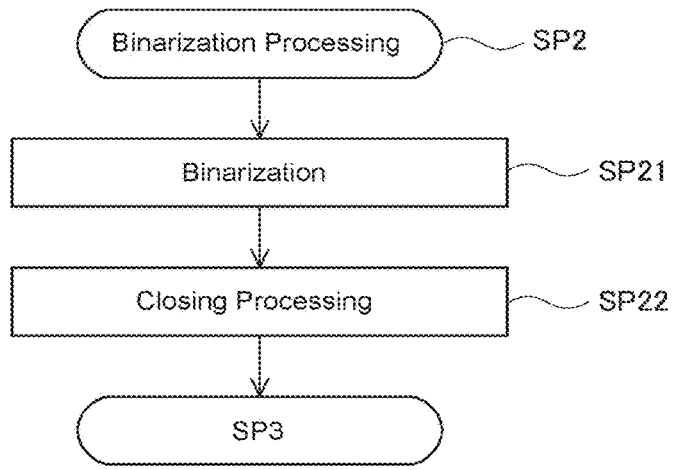
FIG. 4 is a detailed flowchart of binarization processing.

FIG. 4 illustrates a detailed flowchart of binarization processing. The binarization unit 151 firstly creates a binary image by binarizing the X-ray CT image G10, which has been input via the input unit 12, on the basis of a specified threshold value (SP21). Black dot defects may sometimes occur in the created binary image due to uneven density of fibers in the fiber bundles. Specifically speaking, there are some voxels which should originally be the background and are made to become foreground voxels.

In order to make these foreground voxels which should originally be the background return to background voxels, the binarization unit 151 executes closing processing of morphology processing (SP22). The black dot defects which have occurred in the binary image can be eliminated by executing the closing processing. The binarization unit 151 creates a binary image, from which the black dot defects have been eliminated and cleaned, and terminates this processing.

Figure 5:
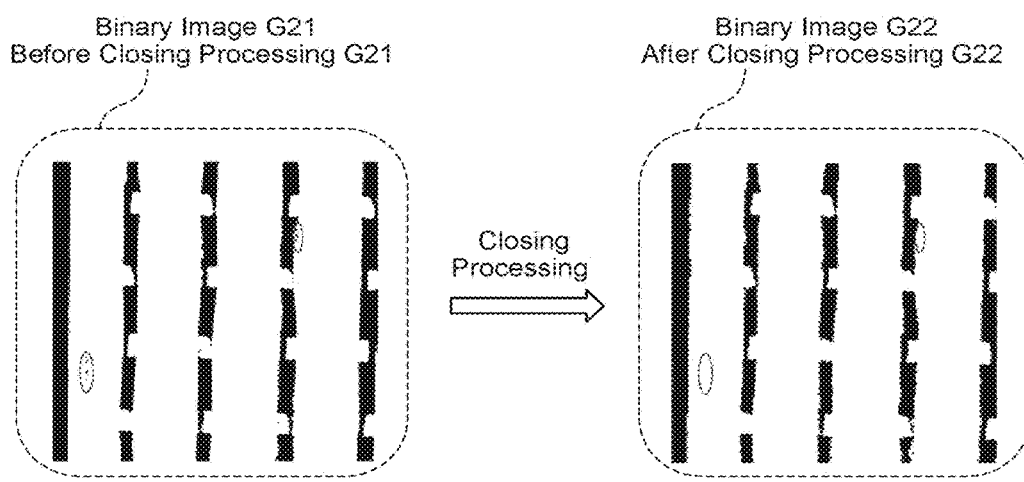
FIG. 5 illustrates processed images created by the binarization processing.

FIG. 5 illustrates processed images created by the binarization processing. Specifically speaking, FIG. 5 illustrates a binary image G21 before the closing processing and a binary image G22 after the closing processing.

The binary image G21 includes some voxels which should originally be the background and are made to become foreground voxels as illustrated in FIG. 5. The binary image G22 after the closing processing, from which the black dot defects have been eliminated, can be obtained by executing the closing processing.

(3-2) Overlapping Area Extraction Processing

Figure 6:
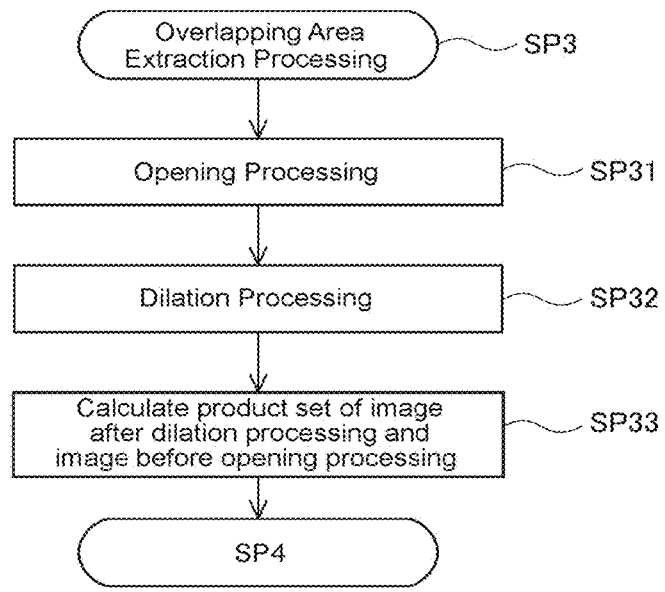
FIG. 6 is a detailed flowchart of overlapping area extraction processing.

FIG. 6 illustrates a detailed flowchart of the overlapping area extraction processing. The overlapping area extraction unit 152 executes opening processing of the morphology processing in order to extract the overlapping area in which the X-yarns and the Y-yarns three-dimensionally intersect with each other (SP31).

A rough overlapping area can be extracted by executing the opening processing. The shape of the binary image after the opening processing has changed and there are some positions where the foreground voxels which should originally be located in the overlapping area are made to become the background voxels in areas that are not the overlapping area.

In order to make these background voxels which should originally be in the overlapping area return to the foreground voxels, the overlapping area extraction unit 152 executes the dilation processing of the morphology processing (SP32).

Next, the overlapping area extraction unit 152 extracts an accurate overlapping area by calculating a product set of the binary image after the dilation processing and the binary image before the opening processing (SP33). The overlapping area extraction unit 152 creates an overlapping area extracted image with the extracted overlapping area and terminates this processing.

Figure 7:
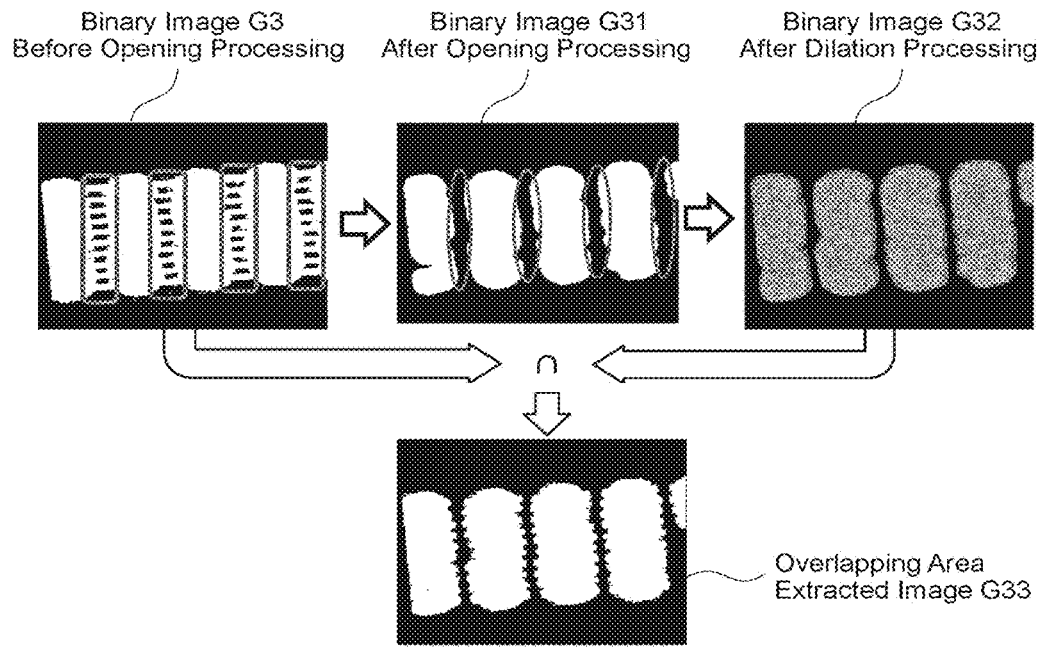
FIG. 7 illustrates processed images created by the overlapping area extraction processing.

FIG. 7 illustrates processed images formed by the overlapping area extraction processing. Specifically speaking, FIG. 7 illustrates a binary image G3 before the opening processing, a binary image G31 after the opening processing, a binary image G32 after the dilation processing, and an overlapping area extracted image G33.

The overlapping area extracted image G33 with the extracted accurate overlapping area can be obtained by calculating a product set of the binary image before the opening processing G3 and the binary image after the dilation processing G32 as illustrated in FIG. 7.

(3-3) Reference Direction Determination Processing

Figure 8:
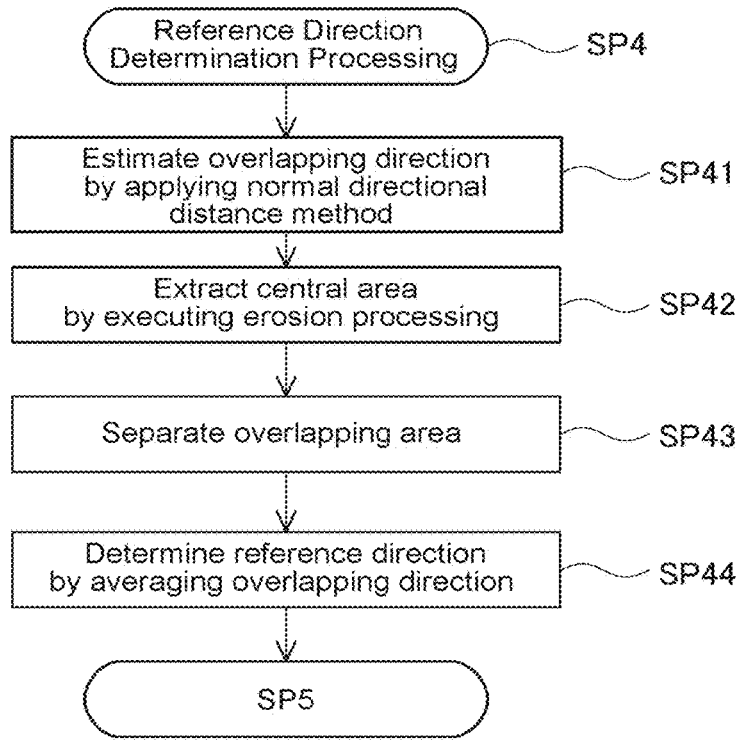
FIG. 8 is a detailed flowchart of reference direction determination processing.

FIG. 8 illustrates a detailed flowchart of reference direction determination processing. The reference direction determination unit 153 applies the normal directional distance method to the overlapping area extracted image G33 (FIG. 7) and estimates the overlapping direction with respect to each voxel in the overlapping area (SP41).

Figure 9:
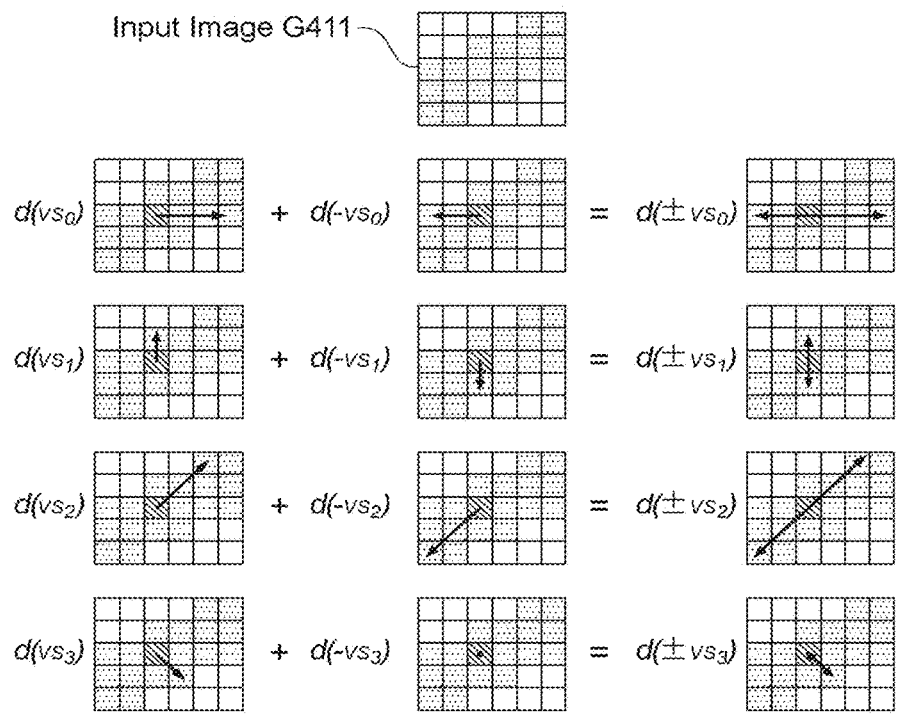
FIG. 9 is a schematic diagram of processing for estimating directional distances by applying a normal directional distance method.

FIG. 9 illustrates the outlines of processing for estimating a directional distance of a voxel of interest by applying the normal directional distance method. When a binarized input image G411 is input, the directional distance to the background is calculated with respect to the voxel of interest. Directions to voxels close to the voxel of interest are eight directions in a case to the two dimensions or 26 directions in a case of the three dimensions.

Now, the case of the two dimensions will be explained. When $vs_i$ represents voxels from which vectors of opposite directions are excluded, the processing proceeds in four directions on the image and stops proceeding when it reaches the background. Similarly, regarding $-vs_i$, the processing proceeds in four directions on the image and stops proceeding when it reaches the background.

When $d(vs_i)$ represents an advanced distance in a $vs_i$ direction and $d(-vs_i)$ represents an advanced distance in a $-vs_i$ direction, a directional distance $d(\pm vs_i)$ in $\pm vs_i$ directions is expressed by Expression 1 below.

[Math. 1]

$$d(\pm vs_i) = d(vs_i) + d(-vs_i) \quad (1)$$

Furthermore, a directional vector $P_i$ and a directional tensor M are defined by Expressions 2 and 3 below, respectively. When eigenvalue decomposition of the directional tensor M is performed, an eigenvector for the maximum eigenvalue indicates the orientation of a fiber bundle. Furthermore, an eigenvector for the second largest eigenvalue indicates a widthwise direction of the fiber bundle. In the case of the three dimensions, an eigenvector for the minimum eigenvalue indicates a thickness direction.

[Math. 2]

$$P_i = d(\pm vs_i) \cdot vs_i \quad (2)$$

[Math. 3]

$$M = \Sigma_{i=0}^{3} P_i P_i^T \; [M = \Sigma_{i=0}^{12} P_i P_i^T \text{ in case of three dimensions}] \quad (3)$$

Referring back to FIG. 8, the overlapping direction estimated in step SP41 is not calculated accurately with respect to voxels in a border region between the overlapping area and the background due to the properties of the directional distance method. In order to remove these voxels in the border region regarding which the calculation cannot be performed accurately, the reference direction determination unit 153 executes erosion processing of the morphology processing and extracts a central area from the overlapping area (SP42).

Next, since each of overlapping areas constitutes an independent connecting component, the reference direction determination unit 153 executes 6-neighbour labeling processing on each extracted central area to divide the area and separates the overlapping areas (SP43).

Subsequently, the reference direction determination unit 153 averages the overlapping directions of the respective voxels in the central area from among the overlapping directions estimated in step SP41, determines the direction obtained by averaging as a reference direction (SP44), and terminates this processing.

Figure 10:
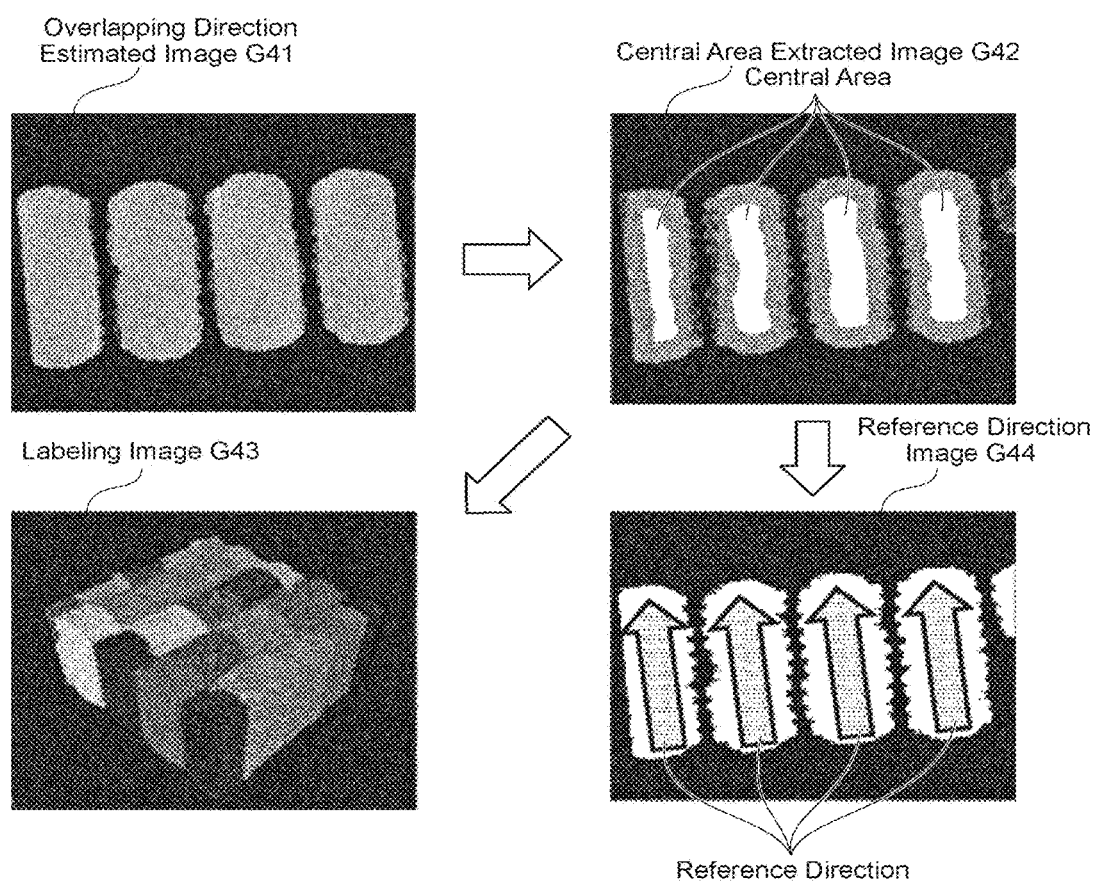
FIG. 10 illustrates processed images created by the reference direction determination processing.

FIG. 10 illustrates processed images created by reference direction determination processing. Specifically speaking, FIG. 10 illustrates an overlapping direction estimated image G41, a central area extracted image G42, a labeling image G43, and a reference direction image G44.

The overlapping direction estimated image G41 can be obtained by applying the normal directional distance method to the overlapping area extracted image G33 (FIG. 7) as illustrated in FIG. 10. Moreover, the central area extracted image G42 can be obtained by executing the erosion processing on the overlapping direction estimated image G41.

Furthermore, the labeling image G43 can be obtained by executing the labeling processing on the central area extracted image G42. Furthermore, the reference direction image G44 can be obtained by averaging the overlapping direction in the central area.

(3-4) Z-yarn Removal Processing

Figure 11:
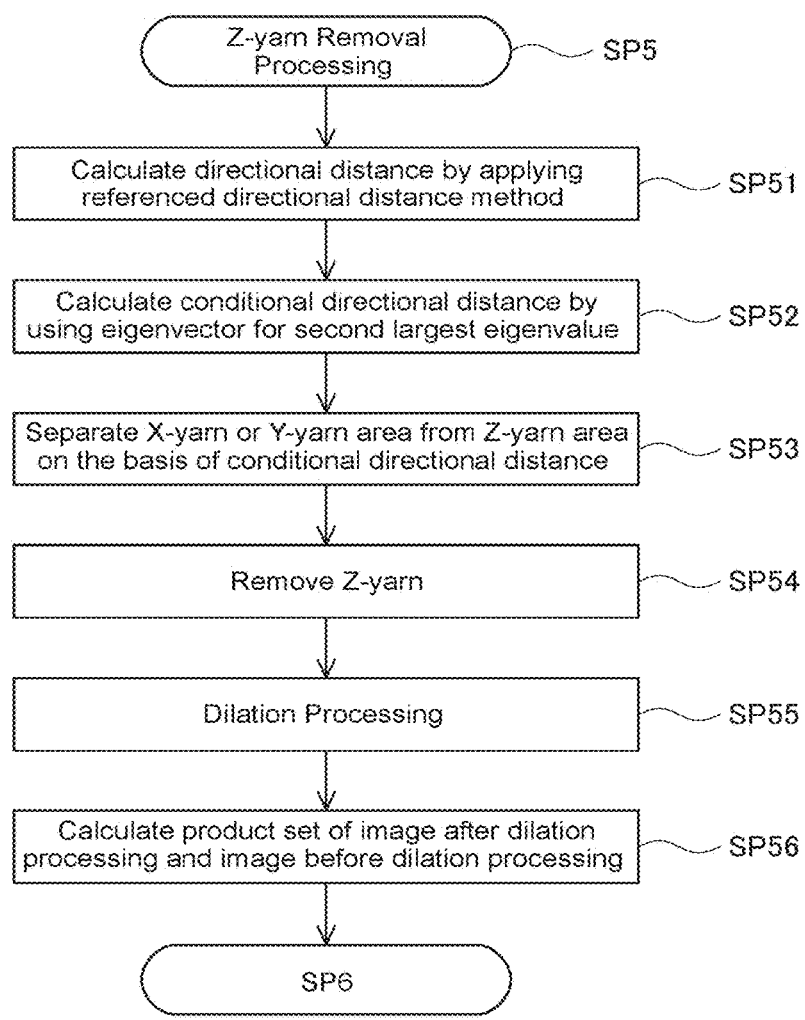
FIG. 11 is a detailed flowchart of Z-yarn removal processing.

FIG. 11 illustrates a detailed flowchart of Z-yarn removal processing. The Z-yarn removal unit 154 calculates the directional distance by applying a referenced directional distance method on the binary image G22 (FIG. 5) obtained in step SP2 (SP51).

The referenced directional distance method is a method for rotating the plane, on which the directional distance is to be calculated, to a plane perpendicular to the reference direction (a reference plane) and calculating the directional distance on this reference plane by the two-dimensional normal directional distance method.

Figure 12:
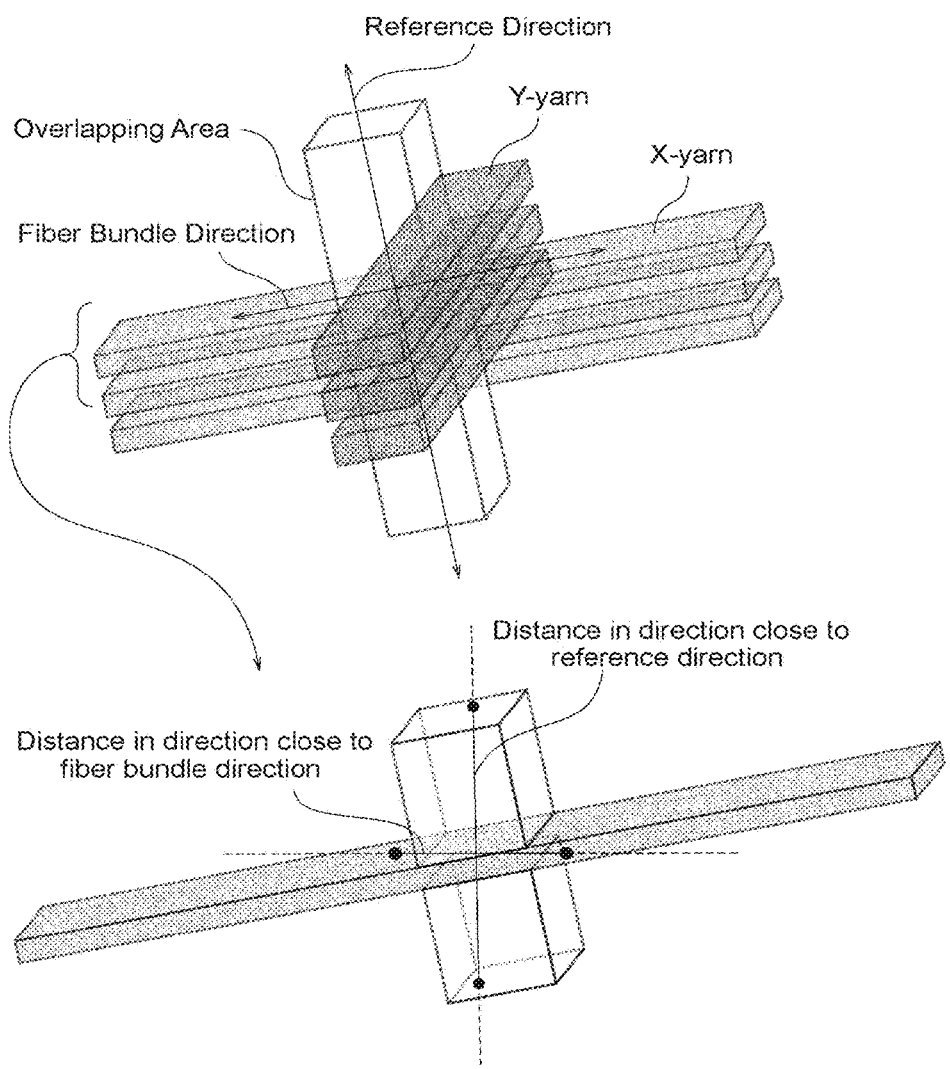
FIG. 12 is a conceptual diagram when the normal directional distance method is applied.

FIG. 12 illustrates a conceptual diagram of a case where the directional distance is calculated by applying the normal directional distance method. When calculating the directional distance in the overlapping area, in which the X-yarns and the Y-yarns three-dimensionally intersect with each other, by applying the normal directional distance method, there is a problem of incapability to calculate the directional distance accurately.

Specifically speaking, the distance in a direction close to the orientation of a fiber bundle shortly reaches the background and becomes short because the thickness of the fiber bundles of the X-yarn and the Y-yarn is thin. On the other hand, the distance in a direction close to the reference direction hardly reaches the background and becomes long because a cross section of the overlapping area is thick.

Therefore, the distance in the direction close to the reference direction becomes longer than the distance in the direction close to the orientation of the fiber bundle. As a result, the problem is that the directional distance in the direction close to the reference direction is calculated as the directional distance in the overlapping area. So, in this embodiment, the directional distance is calculated by applying the referenced directional distance method.

Figure 13:
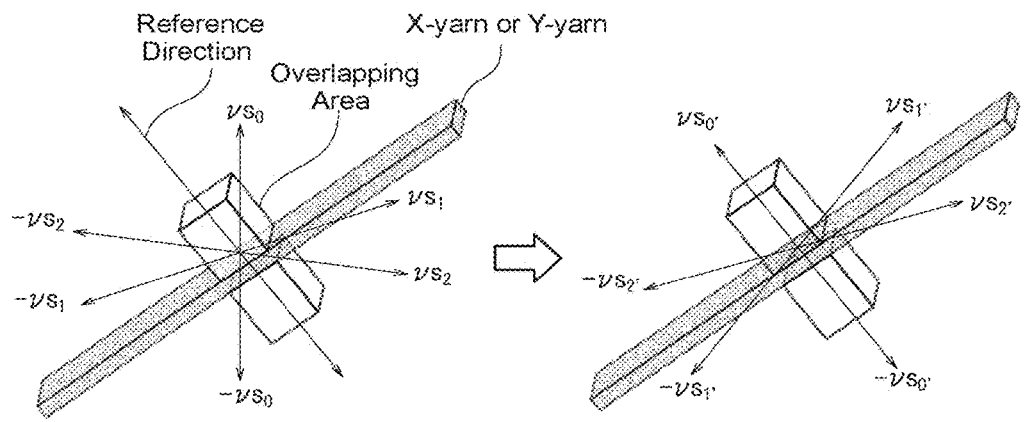
FIG. 13 is a conceptual diagram of a referenced directional distance method.

FIG. 13 illustrates a conceptual diagram of the referenced directional distance method. The referenced directional distance method is a method for rotating the plane which is a target of calculation of the directional distance, and calculating the directional distance by applying the two-dimensional directional distance method on the plane which has been rotated.

Specifically speaking, a direction $\pm vs_0$ is rotated so as to match the reference direction and other directions $\pm vs_1$ and $\pm vs_2$ perpendicular to $\pm vs_0$ are also rotated by the angle of rotation of $\pm vs_0$. When directions obtained after the rotations are expressed as $\pm vs_0'$, $\pm vs_1'$, and $\pm vs_2'$ respectively, the X-yarns or the Y-yarns exist on a plane defined by $\pm vs_1'$ and $\pm vs_2'$ (reference plane).

The orientations of the fiber bundles can be estimated without being influenced by the overlapping area by calculating the directional distance by applying the two-dimensional directional distance method on this reference plane.

Figure 14:
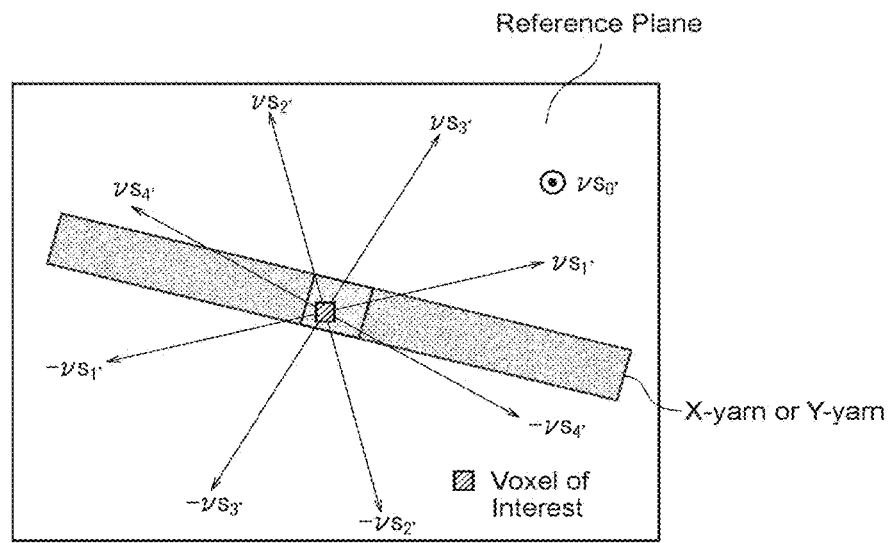
FIG. 14 is a conceptual diagram when the referenced directional distance method is applied.

FIG. 14 illustrates a conceptual diagram in a case where the directional distance of the X-yarns or the Y-yarns on the reference plane is calculated by applying the referenced directional distance method. When calculating the directional distance with respect to a voxel of interest located in the overlapping area, the directional distance is calculated by applying the referenced directional distance method.

Specifically speaking, the direction $\pm vs_0$ is rotated so as to match the reference direction and other directions $\pm vs_1$, $\pm vs_2$, $\pm vs_3$, and $\pm vs_4$ perpendicular to $\pm vs_0$ are also rotated by a similar angle as described above.

When the directions after the rotation are expressed as $\pm vs_0'$, $\pm vs_1'$, $\pm vs_2'$, $\pm vs_3'$, and $\pm vs_4'$ respectively, the directional distance is calculated by applying the two-dimensional directional distance method on the reference plane defined by $\pm vs_1'$, $\pm vs_2'$, $\pm vs_3'$, and $\pm vs_4'$.

The aforementioned relationships indicated by Expressions 1 to 3 are also established when calculating the directional distance by applying the referenced directional distance method. Specifically speaking, when eigenvalue decomposition of the directional tensor M is performed, an eigenvector for the maximum eigenvalue indicates the orientation of a fiber bundle. Furthermore, an eigenvector for the second largest eigenvalue represents a widthwise direction of the fiber bundle. In a case of the three dimensions, an eigenvector for the minimum eigenvalue represents a thickness direction.

Referring back to FIG. 11, the Z-yarn removal unit 154 calculates a conditional directional distance by using the eigenvector for the second largest eigenvalue obtained by the calculation of the referenced directional distance method (SP52). Then, the Z-yarn removal unit 154 separates the X-yarn or Y-yarn area from the Z-yarn area on the basis of the conditional directional distance (SP53).

The conditional directional distance is a directional distance calculated under a condition that the processing stops proceeding when the processing proceeds from a voxel of interest on the image and reaches the background or when an angle formed by a direction indicated by an eigenvector of a voxel at a position, to which the processing will proceed next, and an advancing direction is larger than a specified threshold value.

Figure 15:
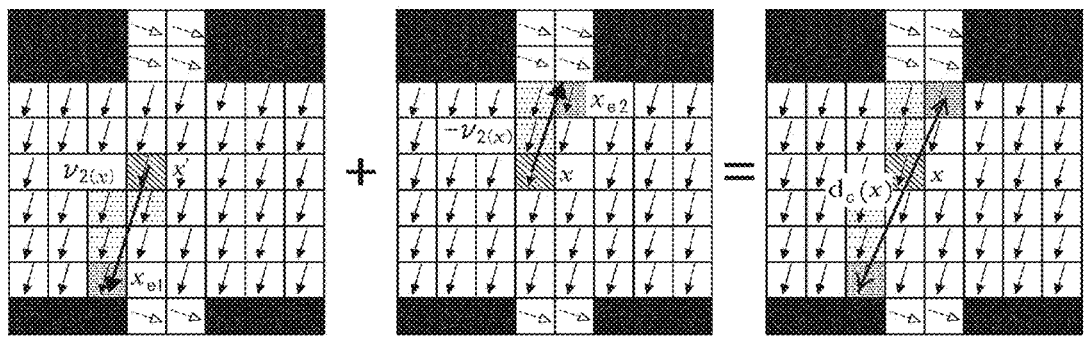
FIG. 15 is a schematic diagram of processing for estimating a conditional directional distance.

FIG. 15 illustrates the outlines of processing for estimating the conditional directional distance. The processing starts at a voxel of interest at position x as a point of origin, proceeds on the image in a direction indicated by an eigenvector $v_2(x)$ for the voxel of interest, and stops proceeding when it reaches the background. The distance from the last reached voxel to the voxel of interest is expressed as $x_{e1}$.

Meanwhile, the processing also proceeds on the image in a direction of an opposite direction vector $-v_2(x)$ and stops proceeding when an angle formed by the direction indicated by an eigenvector $v_2(x')$ for a voxel located at position x', to which the processing will proceed next, and the direction indicated by $-v_2(x)$ is larger than a specified threshold value. The distance from the last reached voxel to the voxel of interest is expressed as $x_{e2}$. Then, a total of absolute values of the distances $x_{e1}$ and $x_{e2}$ is the conditional directional distance $d_c(x)$.

Figure 16:
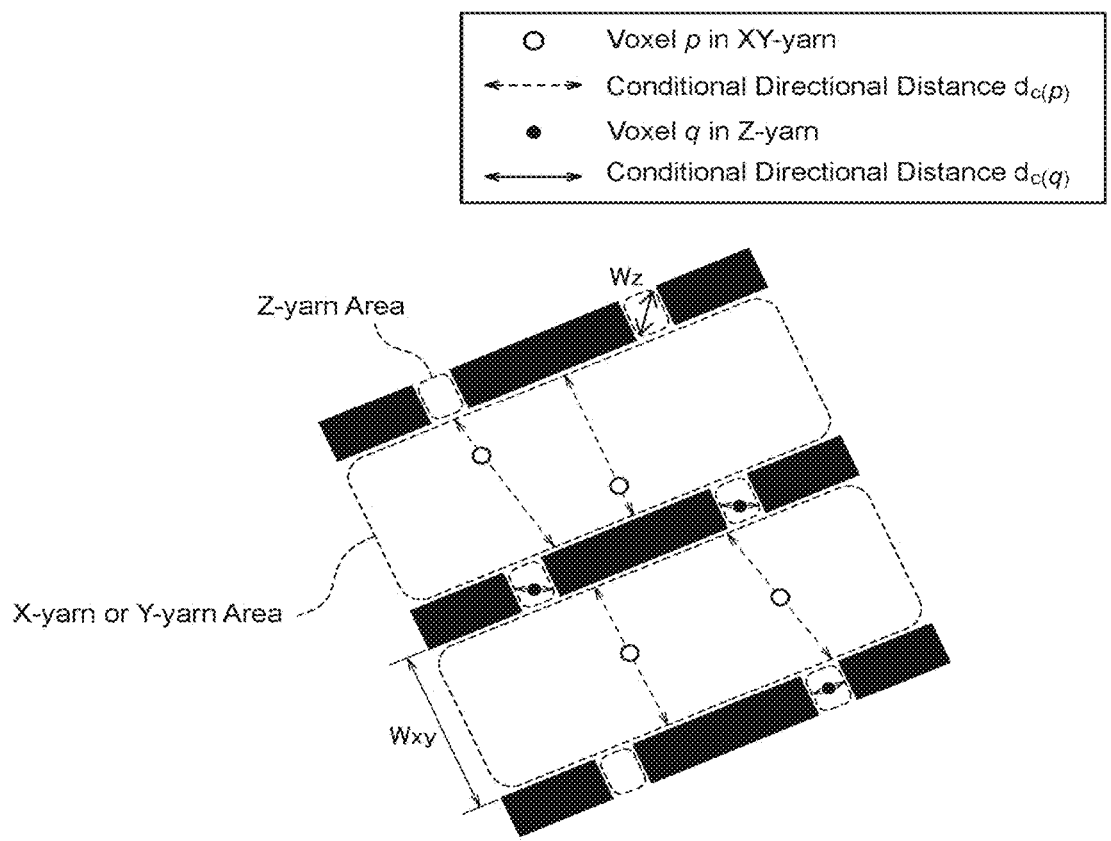
FIG. 16 is a conceptual diagram illustrating X-yarn or Y-yarn areas and Z-yarn areas.

FIG. 16 illustrates a conceptual diagram in which the X-yarn or Y-yarn areas are separated from the Z-yarn areas on the basis of the conditional directional distance. Since the width Wxy of the X-yarn or the Y-yarn is larger than the diagonal distance Wz of the cross section of the Z-yarn, the conditional directional distance $d_c(p)$ of voxel p in the X-yarn or Y-yarn area is larger than the conditional directional distance $d_c(q)$ of voxel q in the Z-yarn area.

For example, a value larger than the diagonal distance Wz of the cross section of the Z-yarn and smaller than the width Wxy of the X-yarn or the Y-yarn can be set as the threshold value, voxels with the conditional directional distance larger than this threshold value can be included in the X-yarn or Y-yarn area, and voxels with the conditional directional distance smaller than the threshold value can be included in the Z-yarn area.

Referring back to FIG. 11, the Z-yarn removal unit 154 removes Z-yarns from the binary image G22 (FIG. 5) by deleting voxels included in the Z-yarn area (SP54). If the Z-yarns are removed, part of the X-yarn or Y-yarn area may sometimes be removed.

So, the Z-yarn removal unit 154: executes dilation processing of the morphology processing on the image from which the Z-yarns have been removed (SP55); extracts the X-yarns and the Y-yarns by calculating a product set of the image after the dilation processing and the image before the dilation processing (SP56); and terminates this processing.

(3-5) Fiber Bundle Orientation Estimation Processing

Figure 17:
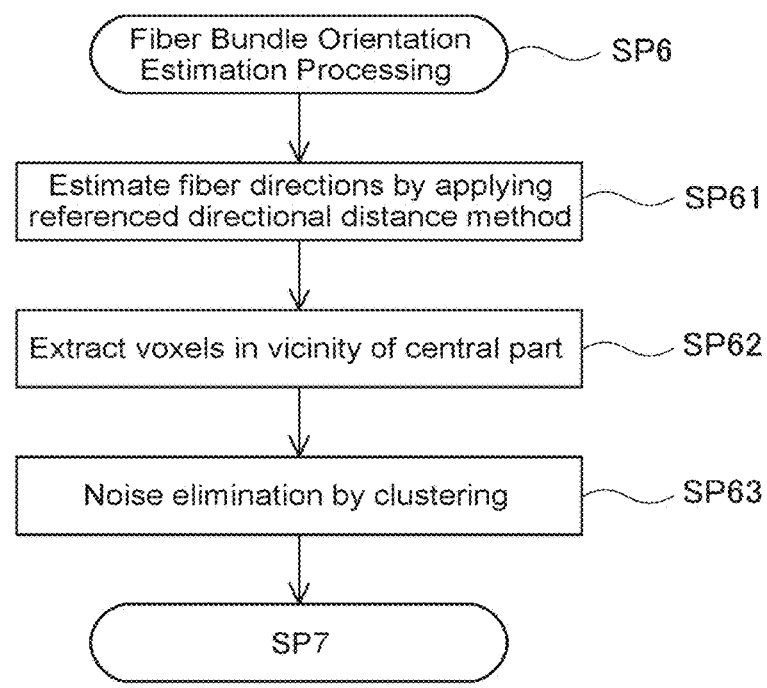
FIG. 17 is a detailed flowchart of fiber bundle orientation estimation processing.

FIG. 17 illustrates a detailed flowchart of fiber bundle orientation estimation processing. The fiber bundle orientation estimation unit 155 estimates the fiber directions of the X-yarns and the Y-yarns by applying the referenced directional distance method again on the image in which the X-yarns and the Y-yarns are extracted (SP61).

Next, the fiber bundle orientation estimation unit 155 deletes other voxels by leaving voxels in the vicinity of a central part with relatively better accuracy, from among the voxels with the estimated fiber directions, thereby extracting the voxels in the vicinity of the central part (SP62).

Subsequently, the fiber bundle orientation estimation unit 155 executes clustering processing in order to connect voxels of similar directions with respect to the voxels in the vicinity of the central part, make the connected group of voxels belong to the same cluster, and make voxels whose vectors suddenly change in the middle of the fiber bundles belong to a different cluster.

The orientation of a fiber bundle does not abruptly change in a short distance of several voxels. Therefore, it is possible to determine that a voxel whose vector abruptly changes in the middle of a fiber bundle is noise. So, the fiber bundle orientation estimation unit 155 eliminates the noise by deleting a cluster to which a small number of voxels belong (SP63), and terminates this processing.

(4) Analysis Results

Processed images obtained when executing the image analysis processing according to this embodiment explained above on various input images will be explained below with reference to FIG. 18 to FIG. 21.

Figure 18:
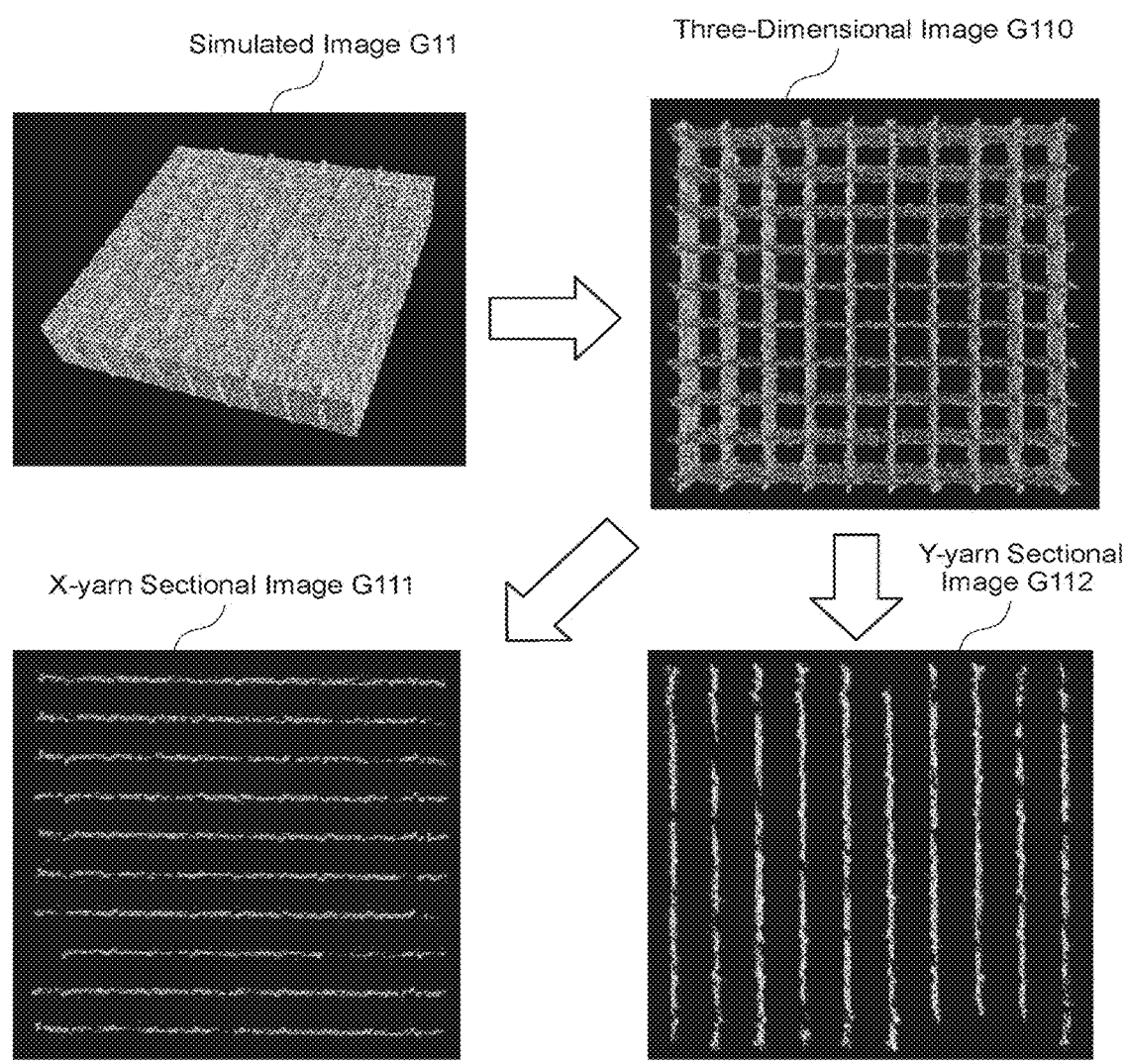
FIG. 18 illustrates analysis results when an input image is a simulated image.

FIG. 18 illustrates processed images obtained by executing the image analysis processing when the input image is a simulated image G11. The simulated image G11 is a three-dimensional image created by setting, for example, the length, width, and thickness of fiber bundles of the X-yarns and the Y-yarns, the number of accumulated X-yarn fiber layers and Y-yarn fiber layers, spaces between the fiber bundles, and a cross-sectional shape of the Z-yarn. In other words, it is an image regarding which various kinds of information are already known.

When the image analysis processing according to this embodiment is executed on this simulated image G11, a three-dimensional image G110, an X-yarn sectional image G111, and a Y-yarn sectional image G112 can be obtained. The three-dimensional image G110 is a three-dimensional image indicating orientations of fiber bundles of the X-yarns and the Y-yarns.

Furthermore, the X-yarn sectional image G111 is a two-dimensional image indicating the orientation of the fiber bundles of the X-yarns; and the Y-yarn sectional image G112 is a two-dimensional image indicating the orientation of the fiber bundles of the Y-yarns.

As a result of calculating an angle formed between the directions of the fiber bundles, which were calculated when obtaining these processed images G110 to G112, and the directions of the fiber bundles which were set when creating the simulated image G11, as an error, the maximum value of the error was 89.9 degrees and an average value was 4.9 degrees.

Incidentally, it is generally known that a mean error of the directional distance method itself is 4.3 degrees. Furthermore, of all the voxels, the error of 94.7% of voxels was 6 degrees or less. The effectiveness of the image analysis processing according to this embodiment can be confirmed on the basis of the above-described results.

Figure 19:
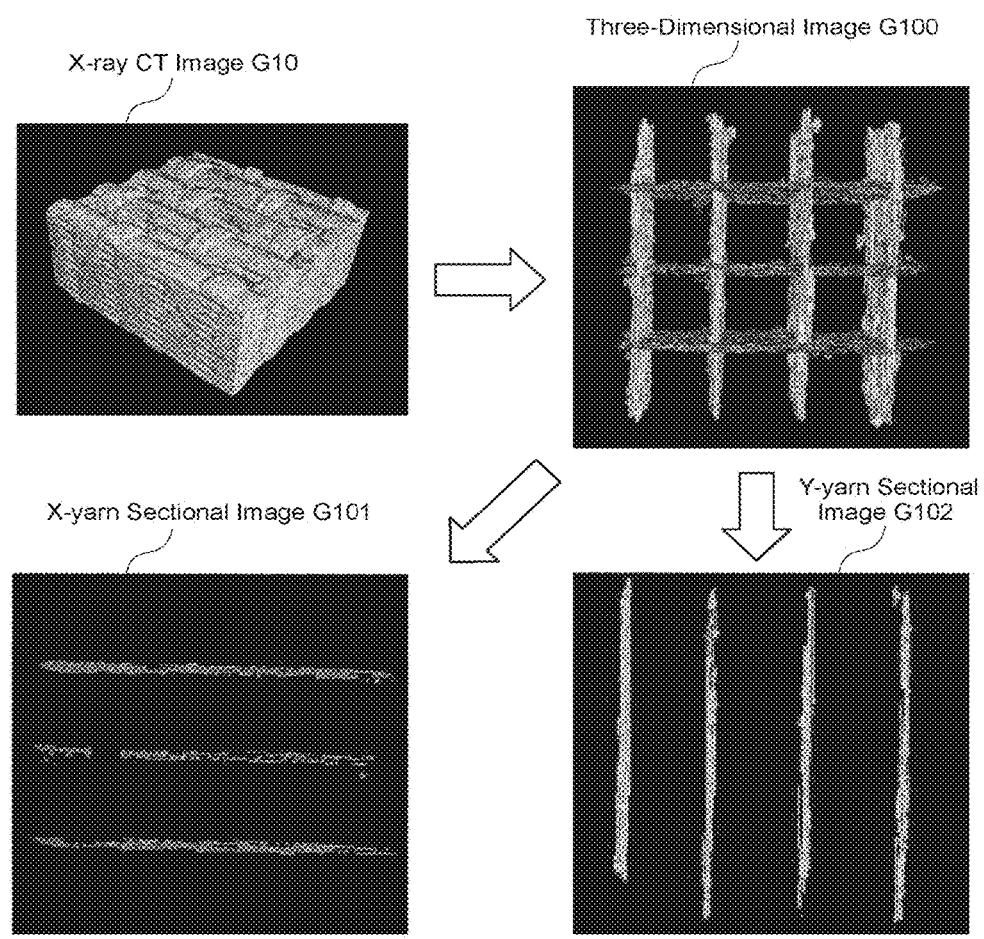
FIG. 19 illustrates analysis results when an input image is a high-definition X-ray CT image.

FIG. 19 illustrates processed images obtained by executing the image analysis processing when the input image is an X-ray CT image G10. The X-ray CT image G10 is a three-dimensional image obtained by capturing an image of an actual woven fabric by using the X-ray CT scanner. Furthermore, the X-ray CT image G10 is of high definition quality as compared to an X-ray CT image G12 illustrated in FIG. 20.

When the image analysis processing according to this embodiment is executed on this X-ray CT image G10, a three-dimensional image G100 (fiber bundle orientation estimated image G100), an X-yarn sectional image G101, and a Y-yarn sectional image G102 can be obtained. The three-dimensional image G100 is a three-dimensional image indicating orientations of fiber bundles of the X-yarns and the Y-yarns.

Furthermore, the X-yarn sectional image G101 is a two-dimensional image indicating the orientation of the fiber bundles of the X-yarns; and the Y-yarn sectional image G102 is a two-dimensional image indicating the orientation of the fiber bundles of the Y-yarns. The orientations of the fiber bundles of the X-yarns and the Y-yarns can be easily identified by referring to these processed image G100 to G102.

Furthermore, calculation time was approximately 243.8 seconds. Conventionally, it takes about 20 times as long as the above-mentioned calculation time in order to analyze an image of approximately the same number of voxels. Therefore, the calculation time can be reduced by executing the image analysis processing according to this embodiment.

Figure 20:
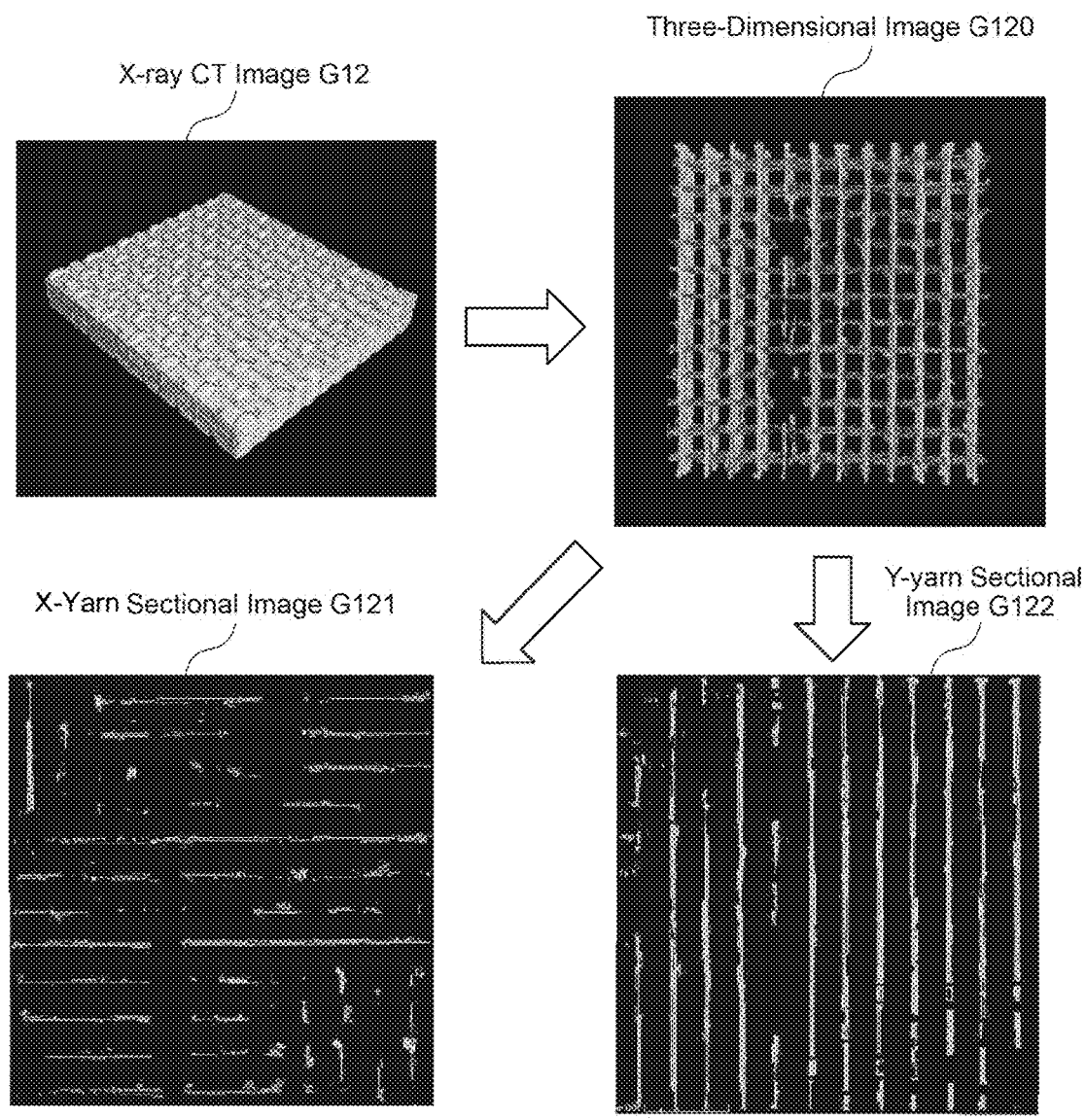
FIG. 20 illustrates analysis results when an input image is a low-definition X-ray CT image.

FIG. 20 illustrates processed images obtained by executing the image analysis processing when the input image is the X-ray CT image G12. The difference between the X-ray CT image G12 and the X-ray CT image G10 illustrated in FIG. 19 is that the X-ray CT image G12 is of low definition quality as compared to the X-ray CT image G10.

When executing the image analysis processing according to this embodiment on this X-ray CT image G12, a three-dimensional image G120, an X-yarn sectional image G121, and a Y-yarn sectional image G122 can be obtained. The orientations of most of the fiber bundles can be easily identified with reference to these processed images G120 to G122 although some parts of the fiber bundles are missing.

Figure 21:
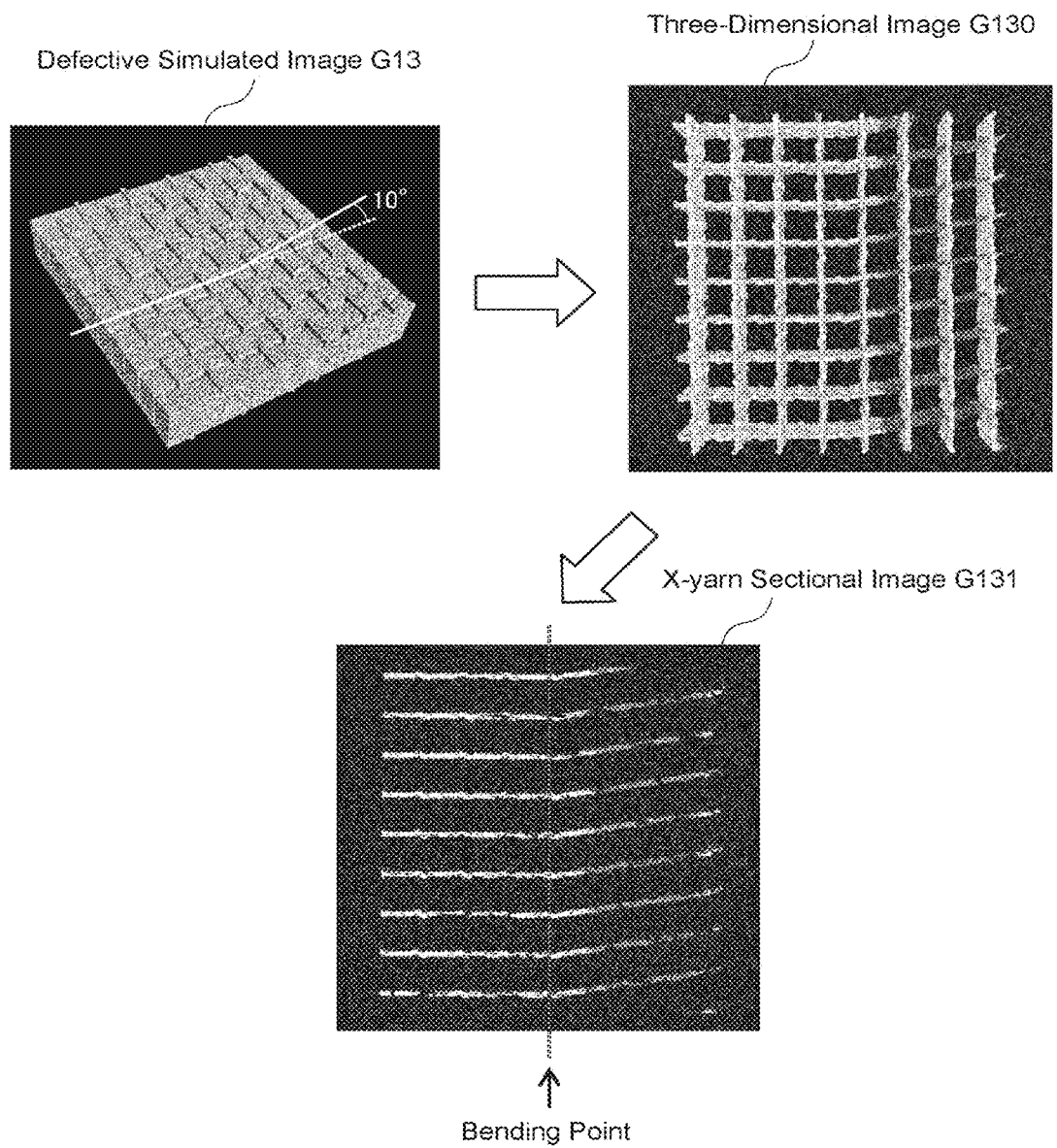
FIG. 21 illustrates analysis results when an input image is a defective simulated image.

FIG. 21 illustrates processed images obtained by executing the image analysis processing when the input image is a defective simulated image G13. The difference between the defective simulated image G13 and the simulated image G11 illustrated in FIG. 18 is that the defective simulated image G13 has a defect in fiber bundles of the X-yarns being bent by 10 degrees in the middle as compared to the simulated image G11.

When executing the image analysis processing according to this embodiment on this defective simulated image G13, a three-dimensional image G130 and an X-yarn sectional image G131 can be obtained. It is possible to easily identify, with reference to these processed images G130 and G131, that fiber bundles of the X-yarns are bent at a bending point although there is some error.

Figure 22:
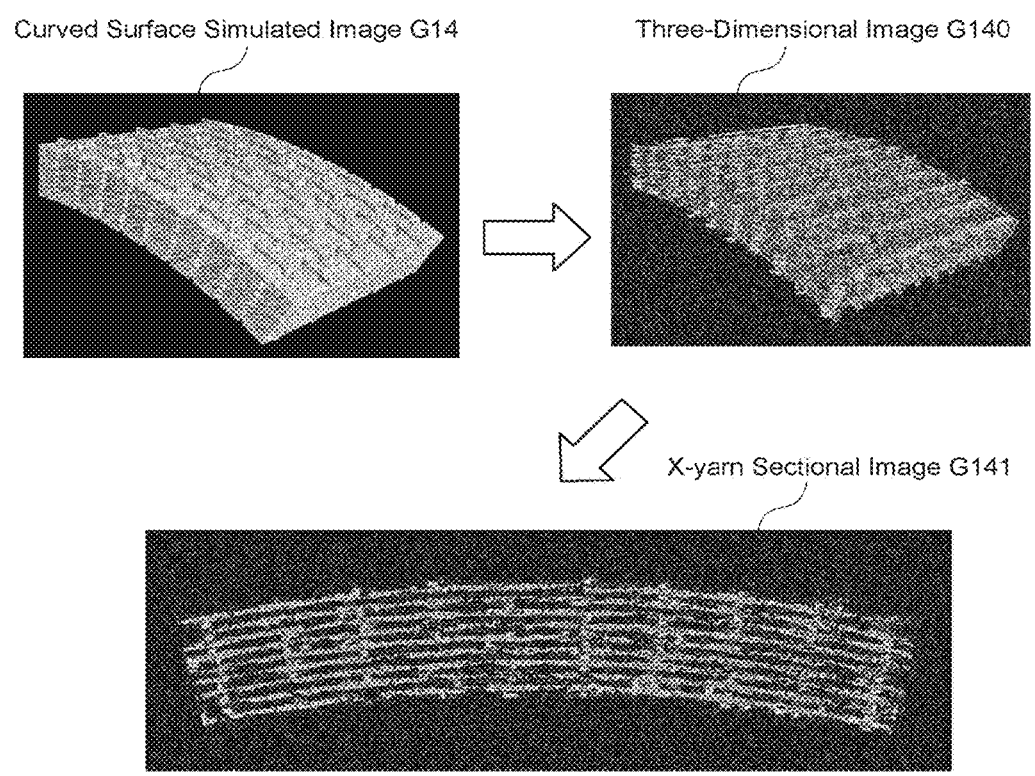
FIG. 22 illustrates analysis results when an input image is a curved surface simulated image.

FIG. 22 illustrates processed images obtained by executing the image analysis processing when the input image is a curved surface simulated image G14. The difference between the curved surface simulated image G14 and the simulated image G11 illustrated in FIG. 18 is that the curved surface simulated image G14 has a curved surface portion deformed in an arc-like shape as compared to the simulated image G11.

When executing the image analysis processing according to this embodiment on this curved surface simulated image G14, a three-dimensional image G140 and an X-yarn sectional image G141 can be obtained. It is possible to easily identify, with reference to these processed image G140 and G141, that the fiber bundles are oriented in an arc.

(5) Advantageous Effects of This Embodiment

The image analysis apparatus, the image analysis method, and the program according to this embodiment is designed as described above to remove the Z-yarns by applying the referenced directional distance method to the X-ray CT image of the woven fabric manufactured by the three-dimensional weaving and estimate the orientations of the fiber bundles of the X-yarns and the Y-yarns by applying the referenced directional distance method again to the image from which the Z-yarns have been removed, so that the orientations of the fiber bundles can be estimated with good accuracy and in a short amount of time by eliminating the influence of the Z-yarns. Furthermore, the orientations of the fiber bundles can be estimated also with respect to the X-ray CT image of the woven fabric having a curved surface shape. Therefore, the image analysis apparatus, the image analysis method, and the program according to this embodiment can be used for actual product examinations.

Next, an image analysis apparatus 2 which is an embodiment of the present disclosure will be explained with reference to FIG. 23 to FIG. 46.

(1) Overall Configuration of Image Analysis Apparatus 2

Figure 23:
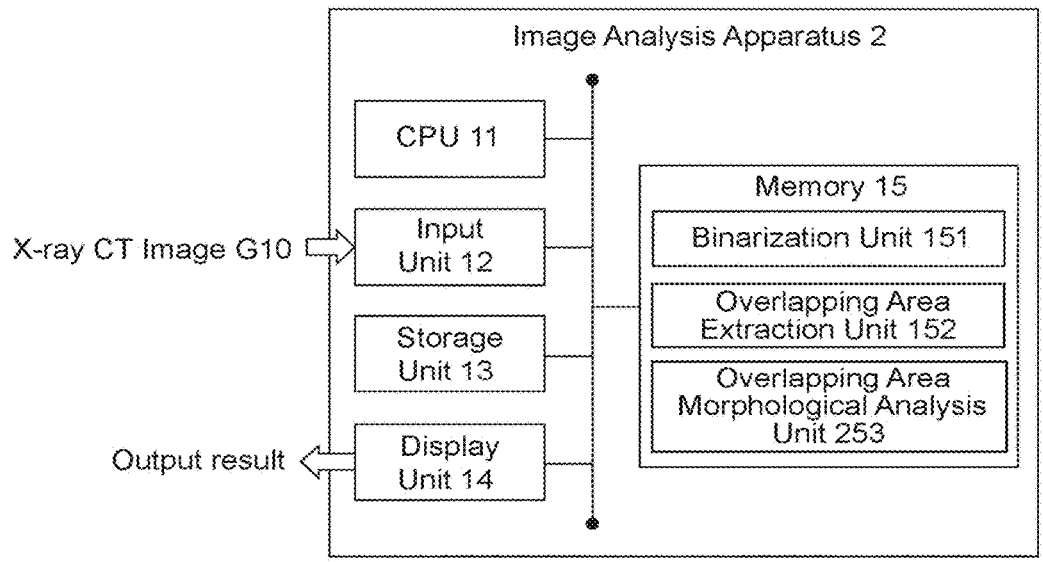
FIG. 23 is an overall configuration diagram of an image analysis apparatus.

The image analysis apparatus 2 according to this embodiment includes, as illustrated in FIG. 23, the CPU 11, the input unit 12, the storage unit 13, the display unit 14, and the memory 15 which are the same as those of the image analysis apparatus 1 in FIG. 1; and the memory 15 has the binarization unit 151 and the overlapping area extraction unit 152. Since these components are the same as those having the same names and reference numerals in FIG. 1 and are designed to execute the same processing, any redundant explanation is omitted. Under this circumstance, the image analysis apparatus 2 according to this embodiment further includes an overlapping area morphological analysis unit 253 in the memory 15. The overlapping area morphological analysis unit 253 analyzes the form of the "overlapping area" in the overlapping area extracted image G33 obtained by the processing of the overlapping area extraction unit 152. Under this circumstance, the form of the overlapping area includes not only the form of one overlapping area, but also the form of a combination of a plurality of overlapping areas which are dotted in the image. Furthermore, the image analysis apparatus 2 has the display unit 14 as illustrated in the drawing, but may be configured to not have the display unit 14 so that it will perform analysis without display.

(2) Flowchart of Image Analysis Processing P2

Figure 24:
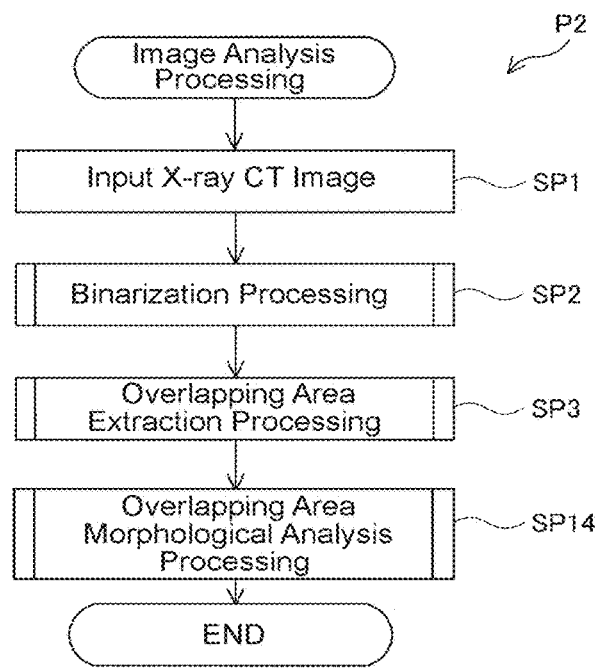
FIG. 24 is an entire flowchart of image analysis processing.

FIG. 24 illustrates a flowchart of image analysis processing P2 executed by the image analysis apparatus 2. The image analysis processing P2 is designed as illustrated in this flowchart to firstly input an X-ray CT image (SP1) and execute binarization processing (SP2) and overlapping area extraction processing (SP3). Since these processing steps are the same as the aforementioned processing of SP1 to SP3 illustrated in FIG. 3, an explanation about them is omitted. Next, during overlapping area morphological analysis processing (SP14), the overlapping area morphological analysis unit 253 executes processing of morphological analysis of an overlapping area 21 by using the overlapping area extracted image G33 (see FIG. 7) obtained by the overlapping area extraction processing. Under this circumstance in this embodiment, individual overlapping areas 21 in the overlapping area extracted image G33 will be hereinafter referred to as "pillars 21".

(3) Examples of Overlapping Area Morphological Analysis Processing

Figure 25:
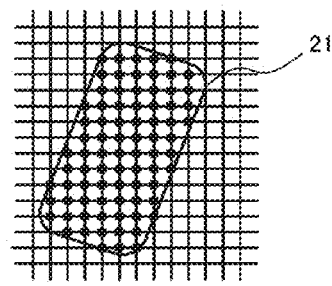
FIG. 25 is a diagram illustrating an example of calculating a volume of a pillar.

The overlapping area morphological analysis unit 253 may calculate the volume of each pillar 21 by, for example, counting the number of voxels included in a three-dimensional image of the pillar 21. FIG. 25 illustrates pixels in a pillar 21, which are indicated as black dots in the two-dimensional image; however, the number of voxels can be counted in the same manner with respect to a three-dimensional image. In this case, whether the volume of a certain pillar 21 is appropriate or not may be judged by, for example, using an average of the volume of a plurality of pillars 21 as a reference value and comparing it with the volume of the certain pillar 21. Under this circumstance, not only the average of the plurality of pillars 21, but also other values such as a reference value in designing may be used as the reference value of the volume. Furthermore, it has been described that the volume of the pillar 21 is calculated; however, in a case of analysis by using a two-dimensional image, the area may be calculated. As a result of such processing for calculating the volume, it is possible to provide useful information for detection of abnormal orientations of the fiber bundles, for example, information indicating that the volume of the certain pillar 21 is different from the volume of surrounding pillars 21. Furthermore, it is possible to detect the abnormal orientation of the fiber bundles, for example, to detect insufficiency in the number of the X-yarns or the Y-yarns which should three-dimensionally interest with each other, on the basis of the provided information.

Figure 26:
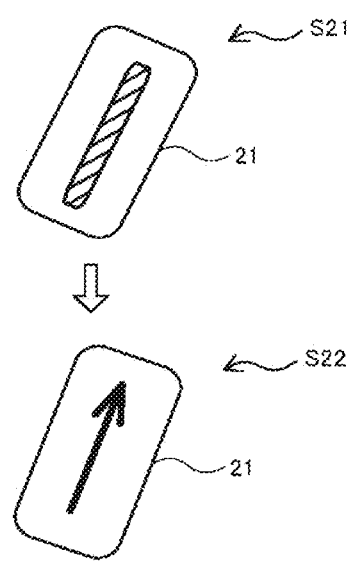
FIG. 26 is a diagram illustrating an example of calculating an extending direction of the pillar.
Figure 27:
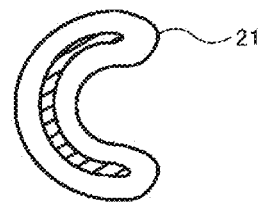
FIG. 27 is a diagram illustrating image processing executed when the pillar is bent.

Furthermore, the overlapping area morphological analysis unit 253 may calculate a direction in which the pillar 21 extends. The extending direction of the pillar 21 may be made visible, for example, as illustrated in FIG. 26 (a shaded area in S21) by using erosion processing of the morphology image processing, and may be vectorized (S22), or the extending direction can be found by using other image processing. Furthermore, for example, the overlapping area morphological analysis unit 253 can judge whether the extending direction of a specified pillar 21 is appropriate or not, by using an average of extending directions of a plurality of pillars 21 as a reference value and comparing it with the extending direction of the specified pillar 21. Under this circumstance, not only the average of the extending directions of the plurality of pillars 21, but also other values such as a reference value in designing may be used as the reference value of the extending direction. Furthermore, a neutral axial shape of the pillar 21 may be found separately from the extending direction of the pillar 21. The neutral axis can be extracted by, for example, using the erosion processing of the morphology image processing as illustrated in the shaded area in FIG. 27. In this case, it is also possible to: detect, for example, a case where the pillar 21 is bent without extending in a certain direction; and further judge whether the pillar 21 is of an appropriate shape or not by comparing it with a reference shape. As a result of such processing for calculating the extending direction or the neutral axis of the pillar 21, it is possible to provide useful information to detect, for example, a displaced portion in the accumulated layers and other problems in the orientations of the fiber bundles. Furthermore, it is possible to detect abnormal orientations of the fiber bundles on the basis of the provided information.

Figure 28:
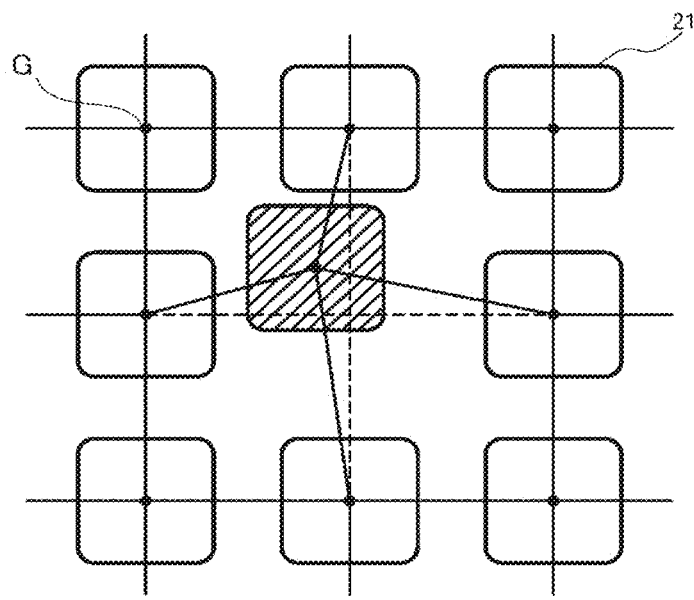
FIG. 28 is a diagram illustrating an example in which pillars are arranged partly irregularly.

Furthermore, the overlapping area morphological analysis unit 253 may calculate centroid positions of a plurality of pillars 21. Since a line connecting centroid positions of adjacent pillars 21 ideally constitutes extending directions of the X-yarns and the Y-yarns, whether the centroid positions are appropriate or not can be judged by finding irregular centroid positions by, for example, detecting that such centroid positions are not aligned along a smooth line on the XY-plane. FIG. 28 illustrates a state where the center of gravity G of a pillar 21 indicated with diagonal lines is not aligned smoothly as compared to the centers of gravity G of surrounding pillars 21. Furthermore, whether a pillar 21 which is irregularly arranged exists or not may be judged by determining a certain area and finding whether an appropriate number of centers of gravity G exist in the area or not by, for example, counting the number of the centers of gravity G in that area. As a result of such processing for calculating the centroid positions, it is possible to provide useful information to detect problems in the orientations of the fiber bundles. Furthermore, it is possible to detect abnormal orientations of the fiber bundles on the basis of the provided information.

The aforementioned example of the overlapping area morphological analysis processing has described the case including the processing for detecting the abnormal orientations of the fiber bundles; however, the processing of the overlapping area morphological analysis unit 253 may be designed to execute only the morphological analysis of the overlapping area such as calculation of the volume of the pillars 21, calculation of the extending directions of the pillars 21, or calculation of the centroid positions of the pillars 21, and may only provide processed information by, for example, outputting the information to the display unit 14 or transmitting calculated data to another apparatus. As a result of such processing, it is possible to provide useful information to detect abnormal orientations of the fiber bundles.

(4) Specific Examples of Abnormal Orientations of Fiber Bundles

Specific examples of abnormal orientations of the fiber bundles detected by the morphological analysis of the pillars 21 will be explained by using FIGS. 29 to 46. Regarding the specific examples of detection of abnormal orientations of the fiber bundles, a case in which the overlapping area morphological analysis processing executed by the overlapping area morphological analysis unit 253 includes detection of abnormal orientations of the fiber bundles will be also described; however, the processing of the overlapping area morphological analysis unit 253 may not include such judgment, but may only provide information about the orientations of the fiber bundles as obtained by the morphological analysis of the pillars 21. Incidentally, FIGS. 30, 33, 36, 38, 40, 41, 43, 44, and 46 are illustrated with reference to a report "DOT/FAA/AR-06/10" issued by FAA (Federal Aviation Administration).

Figure 29:
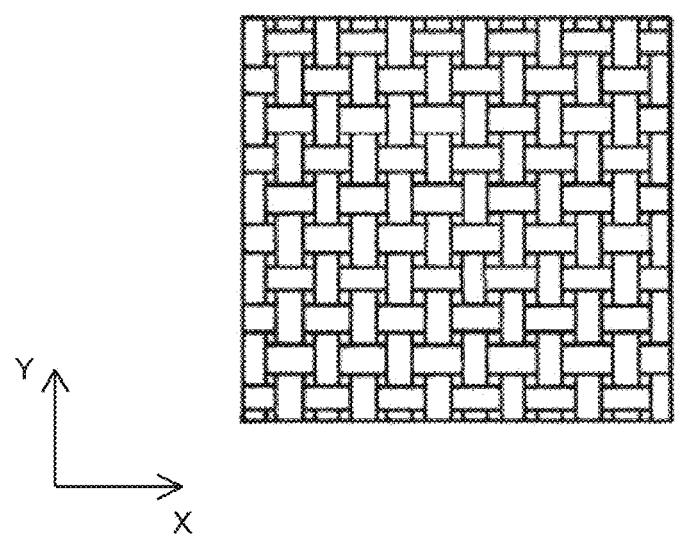
FIG. 29 is a diagram illustrating an ideal arrangement of X-yarn and Y-yarn fiber bundles on an XY-plane.
Figure 30:
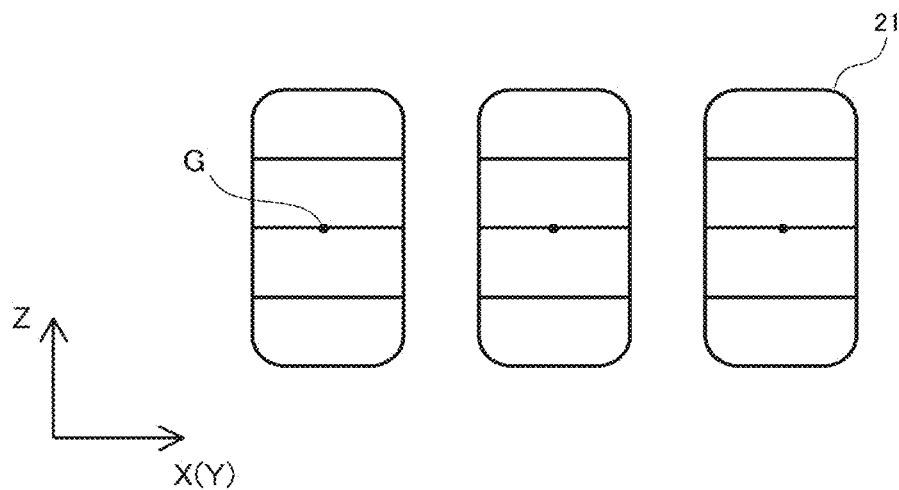
FIG. 30 is a diagram schematically illustrating an overlapping area extracted image on an XZ-plane (or a YZ-plane) in the arrangement of the fiber bundles in FIG. 29.
Figure 31:
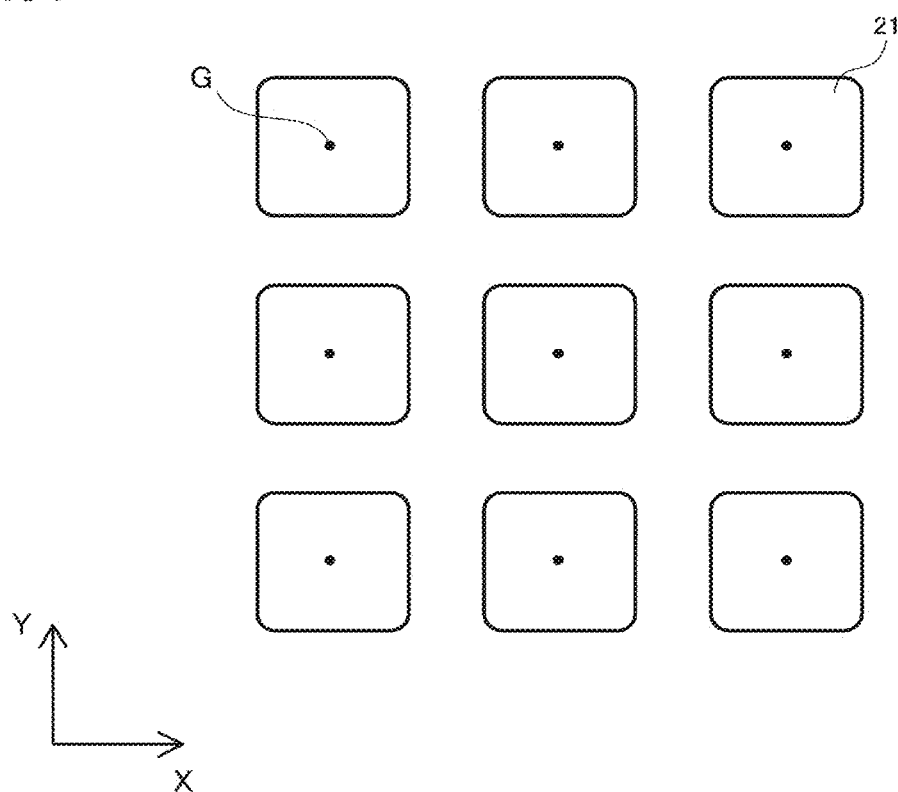
FIG. 31 is a diagram schematically illustrating an overlapping area extracted image on the XY-plane in the arrangement of the fiber bundles in FIG. 29.

FIG. 29 illustrates an example of an ideal arrangement of fiber bundles of the X-yarns and the Y-yarns on the XY-plane; and FIGS. 30 and 31 respectively schematically illustrate overlapping area extracted images on the XZ-plane (or the YZ-plane) and the XY-plane with respect to the ideal fiber bundle arrangement as in FIG. 29. Referring to FIG. 30, a pillar 21 extends without any break in an accumulated direction (Z-direction) of the fiber bundles of the X-yarns and the Y-yarns in the ideal arrangement of the fiber bundles of the X-yarns and the Y-yarns; and referring to FIG. 31, pillars 21 (or the centers of gravity G of the pillars 21) are arranged regularly.

Figure 32:
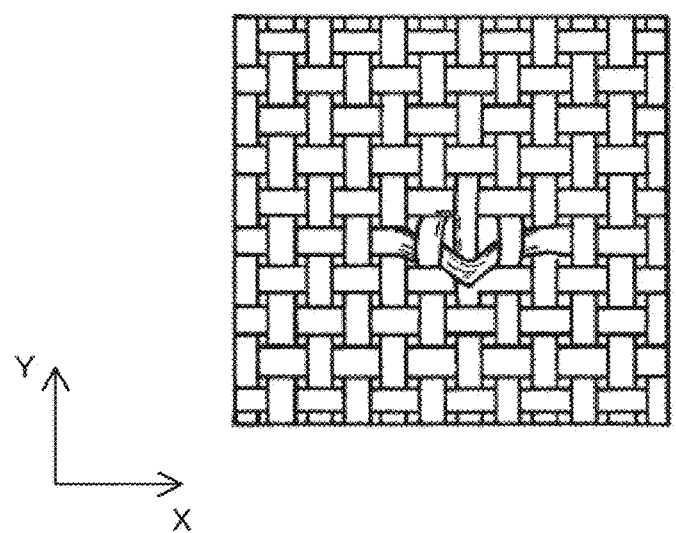
FIG. 32 is a diagram illustrating a state where part of the fiber bundles extends in a direction, on the XY-plane, which is different from a direction it should extend on the XY-plane.
Figure 33:
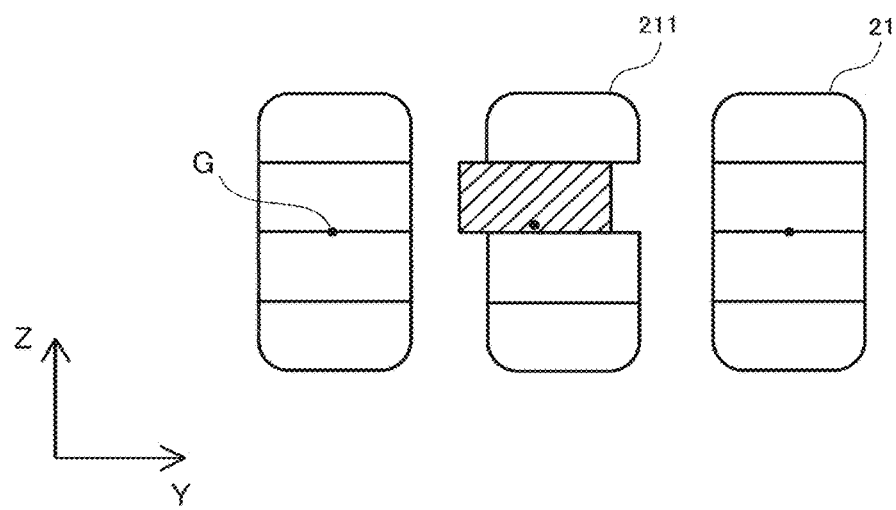
FIG. 33 is a diagram schematically illustrating an overlapping area extracted image on the YZ-plane in the state of the fiber bundles in FIG. 32.
Figure 34:
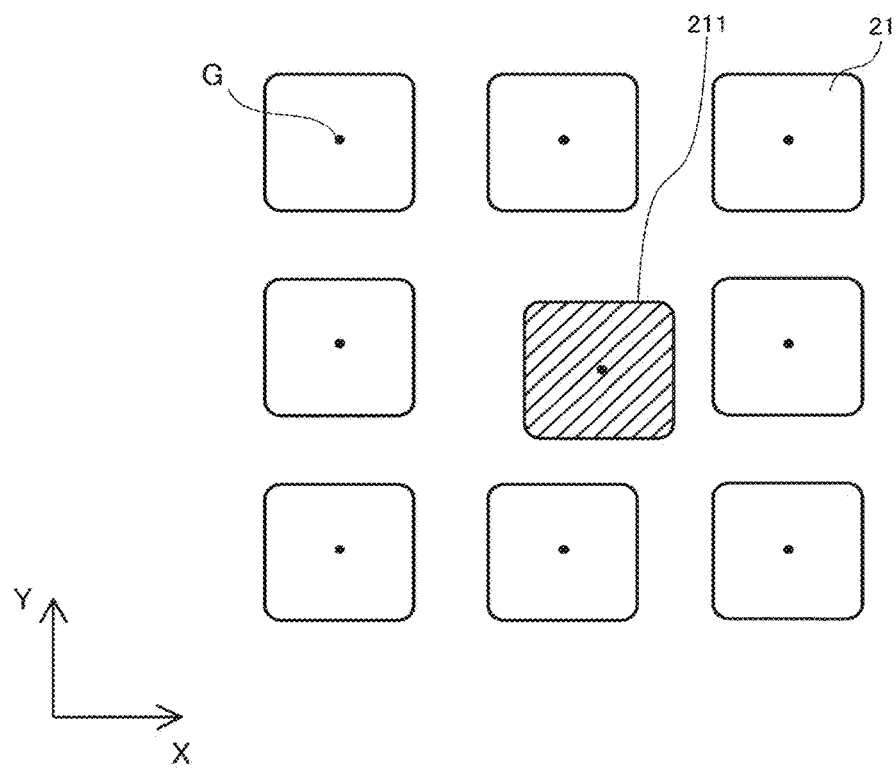
FIG. 34 is a diagram schematically illustrating an overlapping area extracted image on the XY-plane in the state of the fiber bundles in FIG. 32.

FIG. 32 (–Y-direction) illustrates a state on the XY-plane where a portion of a fiber bundle extends in another direction, on the XY-plane, that is different from the direction to which it should extends. FIGS. 33 and 34 respectively schematically illustrate overlapping area extracted images on the YZ-plane and the XY-plane in the state of the fiber bundles in FIG. 32. As illustrated in these diagrams, the centroid position G of a pillar 211 having a fiber bundle extending in the –Y-direction (shaded area) has moved to the –Y-direction due to the influence by that fiber bundle extending in the –Y-direction in the overlapping area extracted image in FIG. 33. Regarding the overlapping area extracted image in FIG. 34, the centroid position G of the pillar 211 does not follow the regularity of the centroid positions of the vicinal pillars 21. Therefore, the overlapping area morphological analysis unit 253 can, for example, analyze the centroid positions G of the respective pillars 21 in the overlapping area extracted image and detects an area where a portion of the fiber bundles extends in another direction, on the XY-plane, different from the direction to which it should extend.

Figure 35:
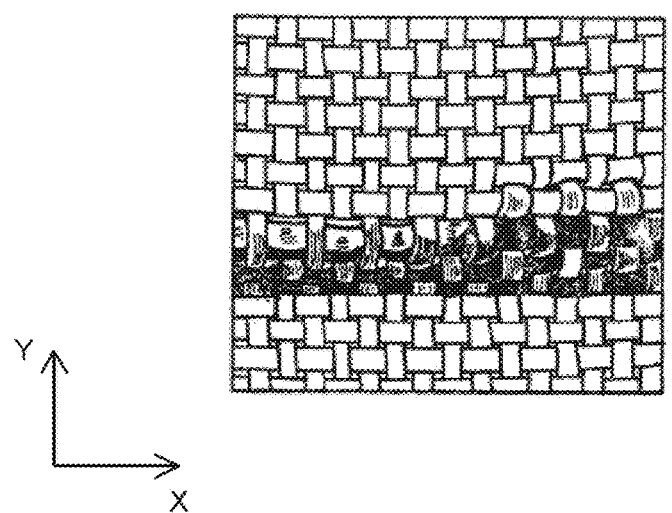
FIG. 35 is a diagram illustrating a state where part of the fiber bundles extends in a Z-direction different from a direction it should extend on the XY-plane.
Figure 36:
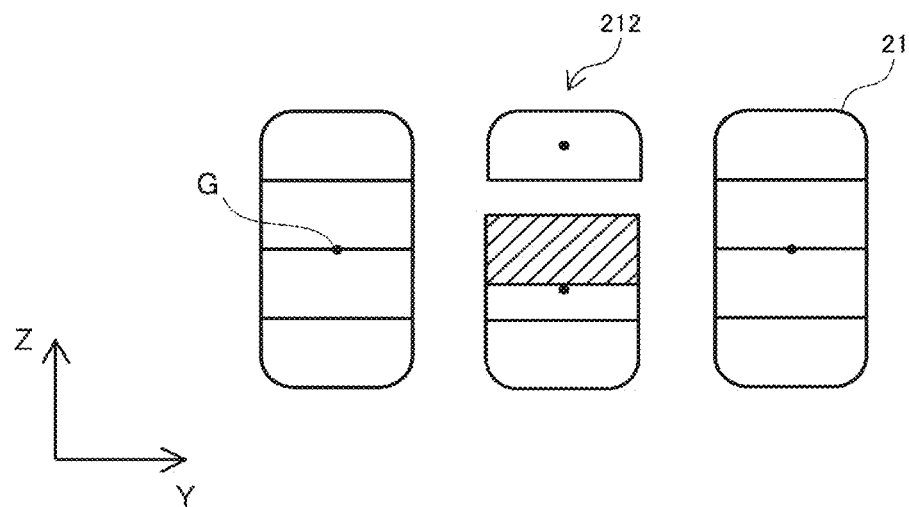
FIG. 36 is a diagram schematically illustrating an overlapping area extracted image on the YZ-plane in the state of the fiber bundles in FIG. 35.

FIG. 35 illustrates a state on the XY-plane where a portion of the fiber bundles extends in the Z-direction different from the direction to which it should extend. FIG. 36 schematically illustrates an overlapping area extracted image on the YZ-plane in the state of the fiber bundles in FIG. 35. As illustrated in this drawing, a pillar 212 in the overlapping area extracted image in FIG. 36 is divided into a plurality of portions due to the influence of the fiber bundle extending in the Z-direction (shaded area). Therefore, the overlapping area morphological analysis unit 253 can detect the area in which a portion of the fiber bundles extends in the Z-direction different from the direction to which it should extend, by using the overlapping area extracted image.

Figure 37:
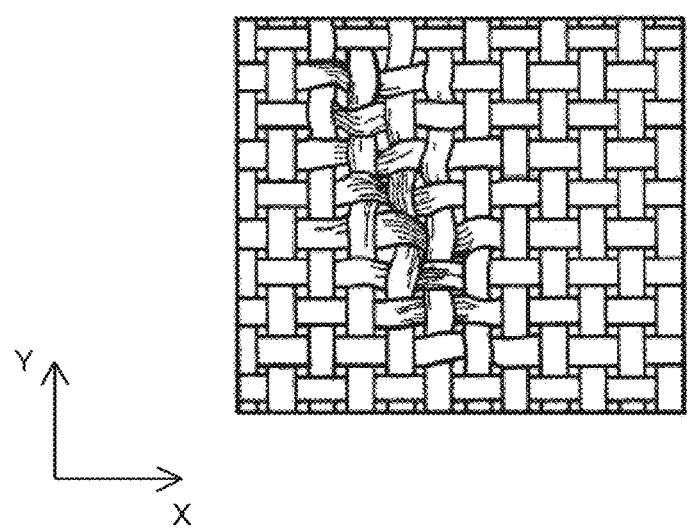
FIG. 37 is a diagram illustrating a state where part of the fiber bundles extends in a direction which is different from a direction it should extend on the XY-plane and which has both a directional component within the XY-plane and a Z-directional component.
Figure 38:
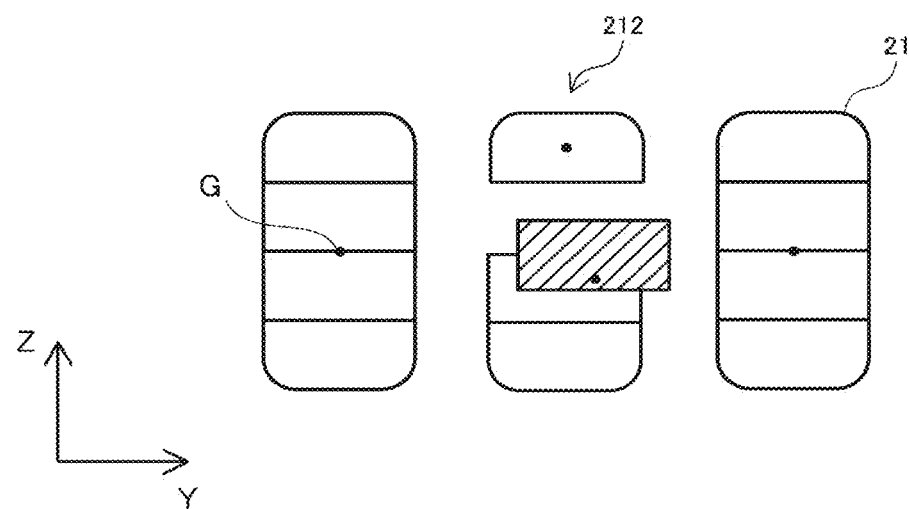
FIG. 38 is a diagram schematically illustrating an overlapping area extracted image on the YZ-plane in the state of the fiber bundles in FIG. 37.

FIG. 37 illustrates a state on the XY-plane where a portion of the fiber bundles extends in a direction that is different from the direction, to which it should extends, and has both a directional component on the XY-plane and a Z-directional component. FIG. 38 schematically illustrates an overlapping area extracted image on the YZ-plane in the state of the fiber bundles in FIG. 37. As illustrated in this drawing, a pillar 213 in the overlapping area extracted image in FIG. 38 is divided into a plurality of portions due to the influence of the fiber bundle extending in the –Z-direction and the –Y-direction (shaded area). Furthermore, the centroid position G of one of the divided pillars 213 has moved to the +Y-direction. Therefore, the overlapping area morphological analysis unit 253 can detect the area in which a portion of the fiber bundles extends in the direction that is different from the direction, to which it should extend, and has both the directional component on the XY-plane and the Z-directional component, by using the overlapping area extracted image.

Figure 39:
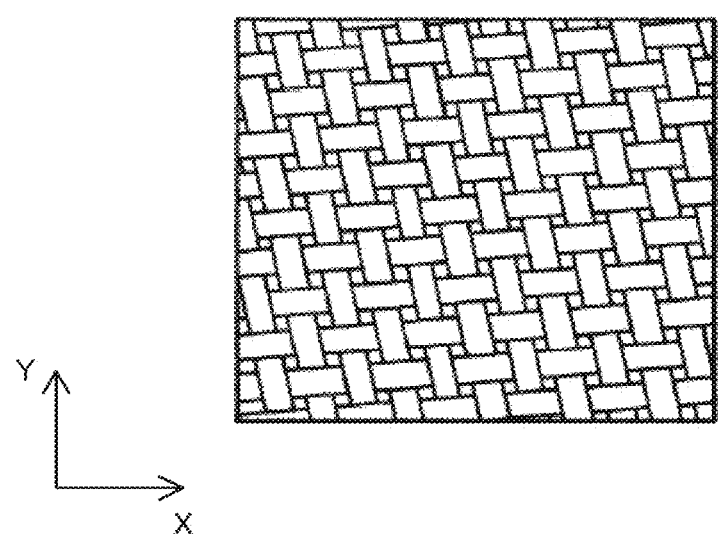
FIG. 39 is a diagram illustrating a state in which the respective fiber bundles extend in tilted directions as a whole on the XY-plane.
Figure 40:
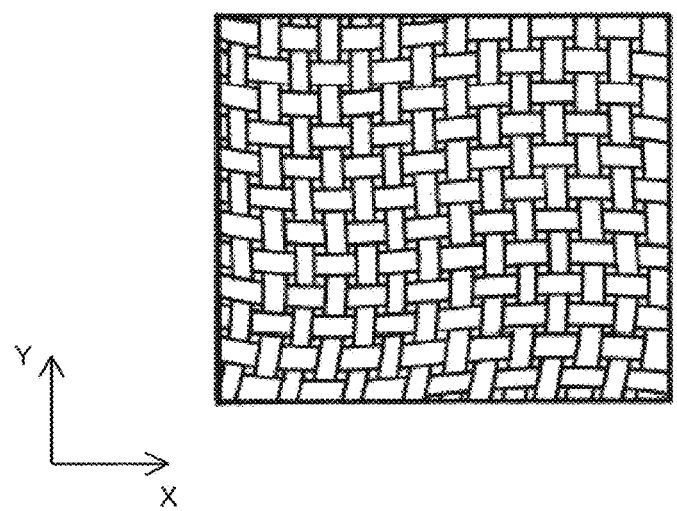
FIG. 40 is a diagram illustrating a state in which the respective fiber bundles extend in tilted directions as a whole on the XY-plane.
Figure 41:
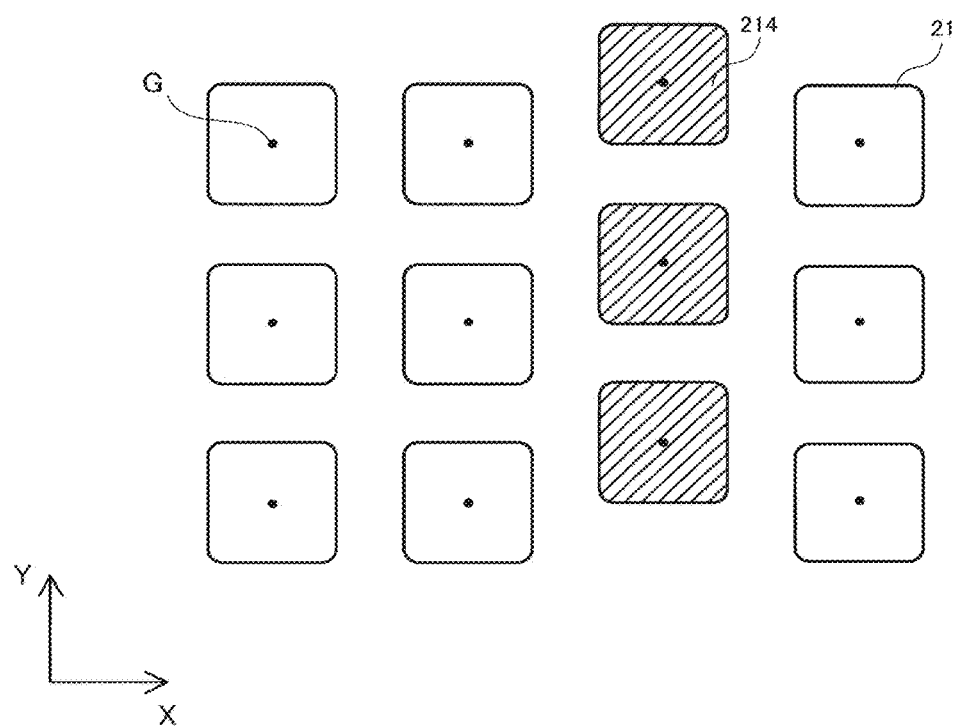
FIG. 41 is a diagram schematically illustrating an overlapping area extracted image on the XY-plane in the state of the fiber bundles in FIG. 39 or 40.

FIGS. 39 and 40 respectively illustrate a state on the XY-plane where the fiber bundles generally extend in inclined directions. FIG. 41 schematically illustrates an overlapping area extracted image on the XY-plane in the state of the fiber bundles illustrated in FIG. 39 or 40. As illustrated in this drawing, pillars 214 which constitute a row that is part of regularly arranged pillars 21 are misaligned in the overlapping area extracted image in FIG. 41. Therefore, the overlapping area morphological analysis unit 253 can detect the area in which the fiber bundles generally extend in the inclined directions, by detecting, for example, that the centroid positions G of the pillars 214 do not follow specified regularity, by using the overlapping area extracted image.

Figure 42:
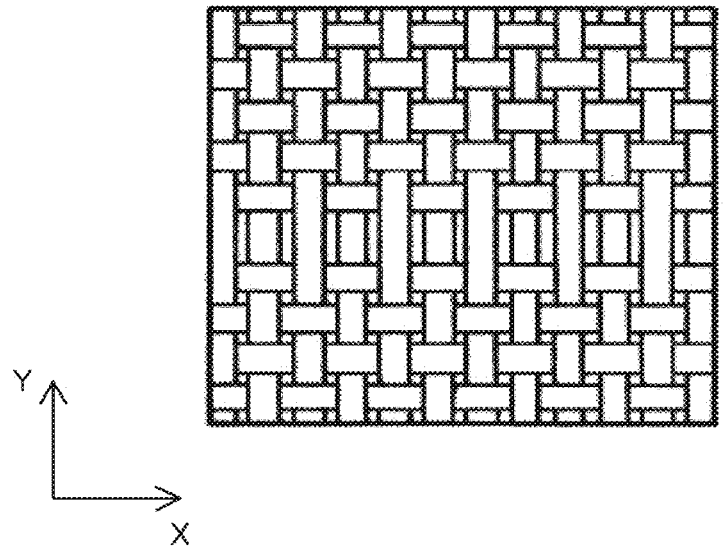
FIG. 42 is a diagram illustrating a state where part of fiber bundles (for example, an X-yarn) is missing on the XY-plane.
Figure 43:
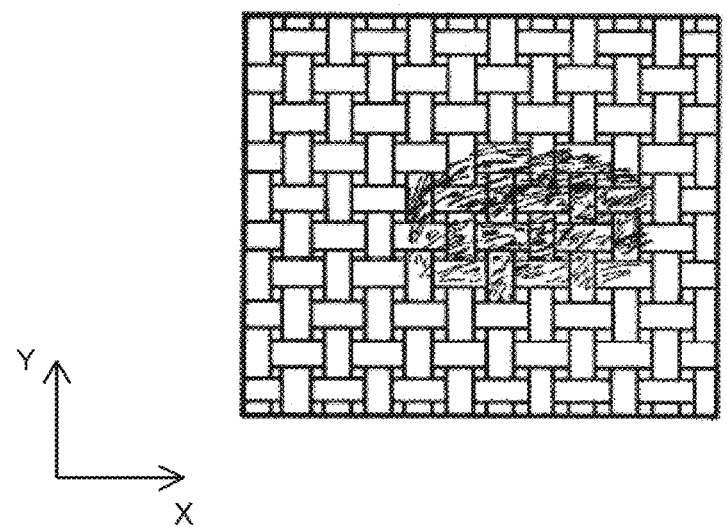
FIG. 43 is a diagram illustrating a state where the thickness of part of the fiber bundles is thicker or narrower than that of other fiber bundles on the XY-plane.
Figure 44:
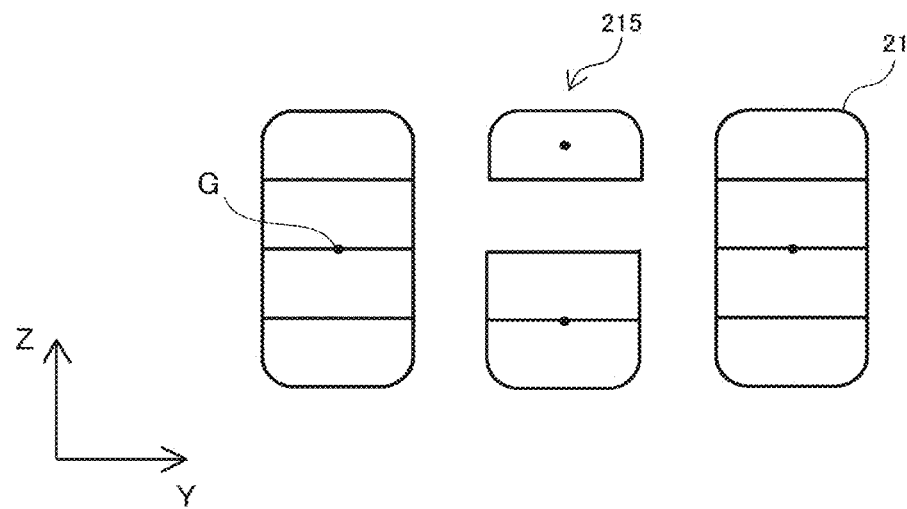
FIG. 44 is a diagram schematically illustrating an overlapping area extracted image on the YZ-plane in the state of the fiber bundles in FIG. 42 or FIG. 43.

FIG. 42 illustrates a state on the XY-plane where a portion of the fiber bundles (for example, an X-yarn) is missing. FIG. 43 illustrates a case where the thickness of a portion of the fiber bundles is thicker or narrower than that of other fiber bundles on the XY-plane. FIG. 44 schematically illustrates an overlapping area extracted image of the YZ-plane in the state of the fiber bundles in FIG. 42 or FIG. 43. Regarding the overlapping area extracted image in FIG. 44, some pillar 215 is divided into a plurality of portions and the total volume of a plurality of divided pillars 215 becomes smaller than the volume of a normal pillar 21. Therefore, the overlapping area morphological analysis unit 253 can detect the case where a portion of the fiber bundle is missing, and the area where the thickness of a portion of the fiber bundles is thicker or narrower than that of other fiber bundles, by using the overlapping area extracted image.

Figure 45:
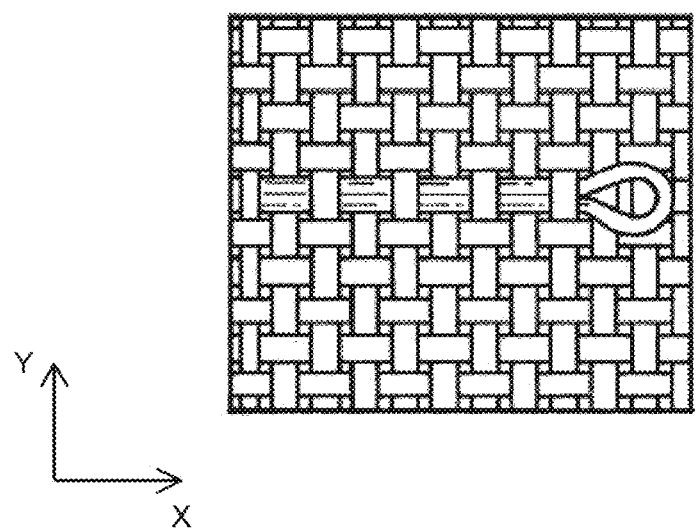
FIG. 45 is a diagram illustrating a state where part of the fiber bundles (such as the X-yarn) is folded back on the XY-plane.

FIG. 45 illustrates a state on the XY-plane where a portion of a fiber bundle (for example, an X-yarn) is folded back.

Figure 46:
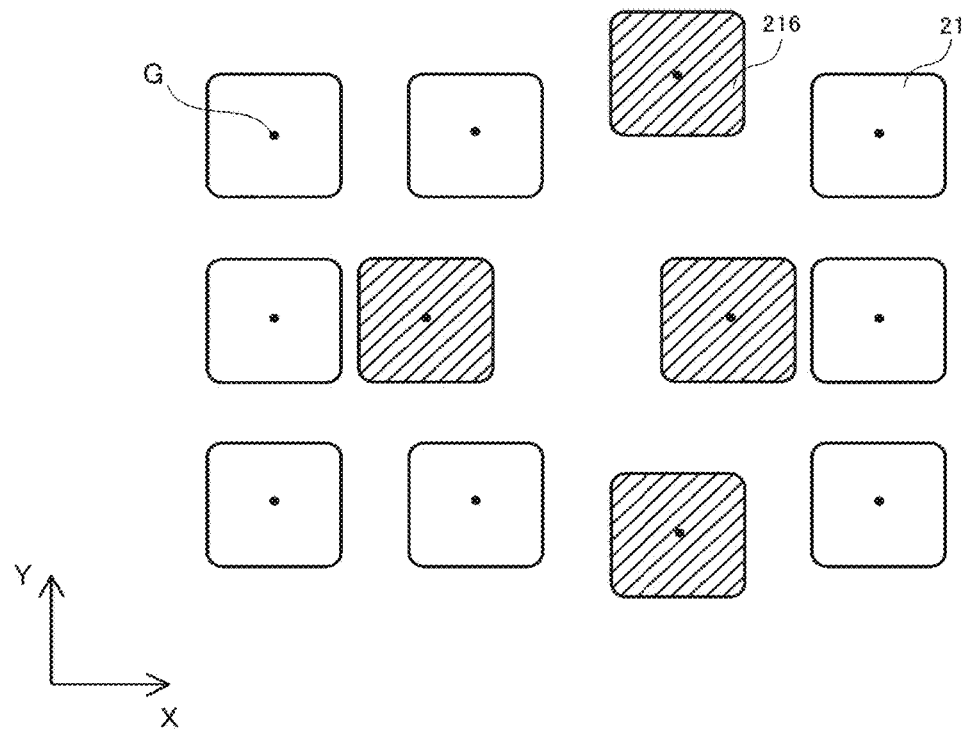
FIG. 46 is a diagram schematically illustrating an overlapping area extracted image on the XY-plane in the state of the fiber bundles in FIG. 45.

FIG. 46 schematically illustrates an overlapping area extracted image of the XY-plane in the state of the fiber bundles in FIG. 45. Regarding the overlapping area extracted image in FIG. 46, pillars 216 surrounding the loop are pushed aside by the loop of the portion of the fiber bundle and the centroid positions G of the pillars 216 are disordered as compared to the centroid positions G of the surrounding regularly-arranged pillars 21. Therefore, the overlapping area morphological analysis unit 253 can detect the area in which a portion of the fiber bundle is looped, by analyzing the disordered arrangement of the centroid positions G by using the overlapping area extracted image.

(5) Advantageous Effects of This Embodiment

The image analysis apparatus 2 according to this embodiment is designed as described above so that: the binarization unit 151 binarizes the three-dimensional image of the woven fabric made of the fiber bundles of the X-yarns, the Y-yarns, and the Z-yarns; the overlapping area extraction unit 152 extracts the overlapping area, in which the X-yarns and the Y-yarns three-dimensionally intersect with each other, from the binarized image; and the overlapping area morphological analysis unit 253 analyzes the form of the extracted overlapping area. As a result, the analysis is performed by only a combination of image processing in a short amount of processing time, so that it is possible to provide information about the orientations of the fiber bundles of the X-yarns and the Y-yarns more easily and in a shorter amount of time.

Furthermore, when the overlapping area morphological analysis unit 253 further detects abnormal orientations of the fiber bundles, it is possible to find the abnormal orientations of the fiber bundles more easily and in a shorter amount of time. Furthermore, even when detailed analysis of the abnormal orientations of the fiber bundles is required, it is only necessary to separately perform the detailed analysis only with respect to the area including the detected abnormal orientations. So, analysis time can be shortened as a whole.

Furthermore, the morphological analysis of the overlapping area according to this embodiment can be employed regardless of whether the general shape of the entire fiber bundles is a flat surface or a curved surface. Since the overlapping area can be extracted no matter what general shape the fiber bundles is, the overlapping area morphological analysis processing can be applied. Furthermore, since the pillars 21 are arranged regularly over the general shape of the fiber bundles, for example, problems of the orientations of the fiber bundles can be also detected by analyzing the form of the overlapping area regardless of whether the general shape of the fiber bundles is a flat surface or a curved surface.

Furthermore, the overlapping area morphological analysis unit 253 may calculate the volume of the overlapping area. In this case, the volume of the overlapping area can be compared with a "reference volume value" of the overlapping area; and furthermore, this "reference volume value" can be an average value of the volume of a plurality of overlapping areas.

Furthermore, the overlapping area morphological analysis unit 253 may calculate the direction in which the overlapping area extends. In this case, the direction in which the overlapping area extends can be compared with a "reference direction value" of the overlapping area; and this "reference direction value" can be an average value of the directions of the plurality of overlapping areas.

Furthermore, the overlapping area morphological analysis unit 253 may calculate centroid positions of the plurality of overlapping areas. In this case, the overlapping area morphological analysis unit 253 can detect an area where the centroid positions are arranged irregularly. For example, the area where the centroid positions are arranged irregularly may be detected by, for example, finding a reference line where the centroid positions are aligned and calculating how much the relevant centroid position(s) is displaced from the reference line, or by calculating the number of centroid positions included in a certain area.

Furthermore, the overlapping area morphological analysis unit 253 may calculate the neutral axis of the overlapping area and compare it with a reference shape. In this case, the erosion processing of the morphology can be used to calculate the neutral axis.

Furthermore, the image analysis method according to this embodiment is an image analysis method that includes: a step of binarizing a three-dimensional image of the woven fabric made of the fiber bundles of the X-yarns, the Y-yarns, and the Z-yarns; a step of extracting an overlapping area, in which the X-yarns and the Y-yarns three-dimensionally intersect with each other, from the binarized image; and a step of analyzing the form of the extracted overlapping area.

Furthermore, the program according to this embodiment is a program for causing a computer to execute: a step of binarizing a three-dimensional image of the woven fabric made of the fiber bundles of the X-yarns, the Y-yarns, and the Z-yarns; a step of extracting an overlapping area, in which the X-yarns and the Y-yarns three-dimensionally intersect with each other, from the binarized image; and a step of analyzing the form of the extracted overlapping area.

(6) Other Embodiments

Figure 47:
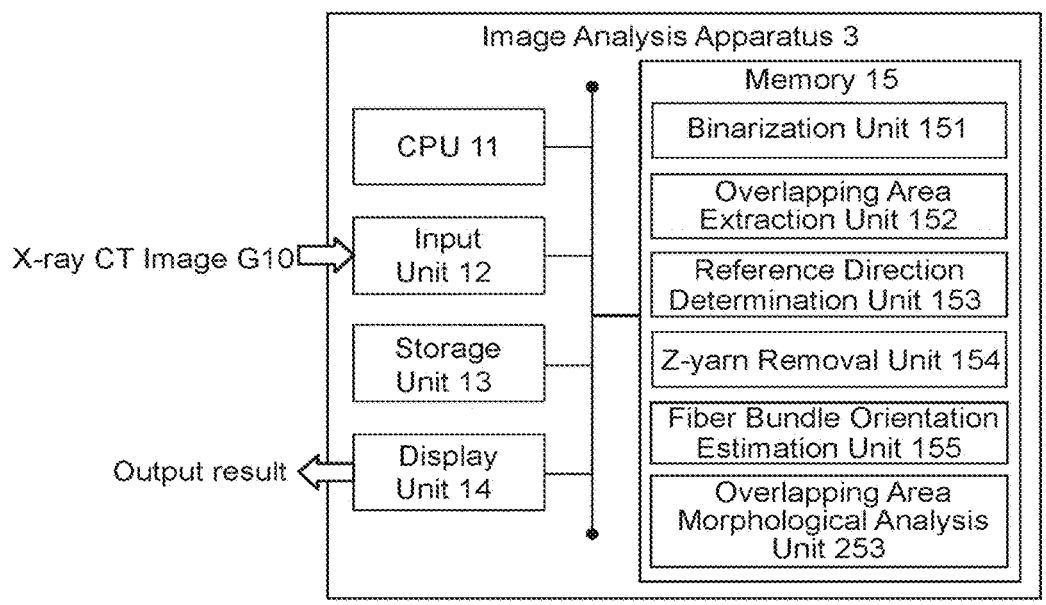
FIG. 47 is an overall configuration diagram of an image analysis apparatus.

Each of the above-described embodiments have described the case where the image analysis processing (FIG. 3) by the image analysis apparatus 1 illustrated in FIG. 1 and the image analysis processing P2 (FIG. 24) by the image analysis apparatus 2 illustrated in FIG. 23 are used separately; however, they can be made to operate in association with each other. FIG. 47 illustrates the configuration of an image analysis apparatus 3 which is one of embodiments for executing these processing steps by combining them. The image analysis apparatus 3 includes the CPU 11, the input unit 12, the storage unit 13, the display unit 14, and the memory 15 in the same manner as the aforementioned image analysis apparatus 1 or 2; and the memory 15 has the binarization unit 151, the overlapping area extraction unit 152, the reference direction determination unit 153, the Z-yarn removal unit 154, the fiber bundle orientation estimation unit 155, and the overlapping area morphological analysis unit 253. Each component executes the same processing as that of the aforementioned corresponding component.

Figure 48:
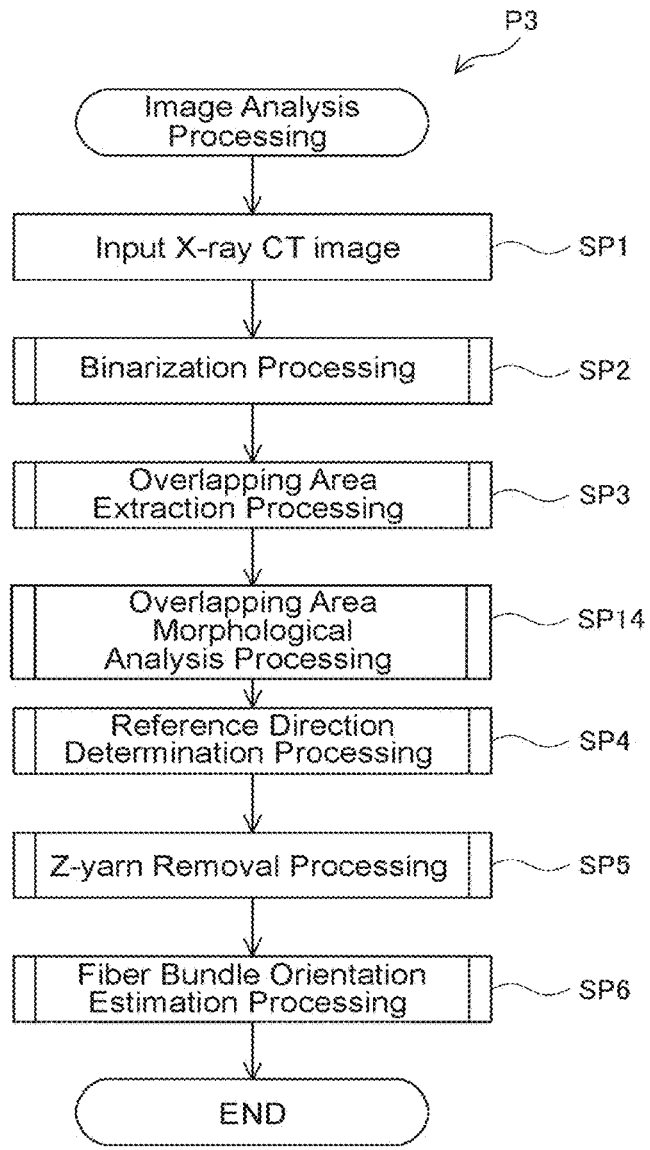
FIG. 48 is an entire flowchart of the image analysis processing.

FIG. 48 illustrates a flowchart of image analysis processing P3 by this image analysis apparatus 3. In the same manner as the image analysis processing P2 in FIG. 24, the image analysis processing P3 firstly inputs an X-ray CT image (SP1) and executes binarization processing (SP2), overlapping area extraction processing (SP3), and overlapping area morphological analysis processing (SP14). Under this circumstance, during the overlapping area morphological analysis processing, not only the form of the overlapping area is analyzed, but also an abnormal orientation of fiber bundles is detected. Next, in the same manner as the corresponding processing of the image analysis processing P1 in FIG. 3, reference direction determination processing (SP4), Z-yarn removal processing (SP5), and fiber bundle orientation estimation processing (SP6) are executed on an area including the detected abnormal orientation of the fiber bundles.

In this way, the problem in the orientation of the fiber bundles can be analyzed more efficiently and in detail by applying the image analysis processing P2, whose processing time is short, to, for example, the X-ray CT image which is the examination target, and applying the image analysis processing P1, whose processing time is relatively long and which performs detailed analysis, on the area including the abnormal orientation of the fiber bundles which is detected by the image analysis processing P2.

REFERENCE SIGNS LIST 1 image analysis apparatus
11 CPU
12 input unit
13 storage unit
14 display unit
15 memory
151 binarization unit
152 overlapping area extraction unit
153 reference direction determination unit
154 Z-yarn removal unit
155 fiber bundle orientation estimation unit
2 image analysis apparatus
21 pillar
253 overlapping area morphological analysis unit
3 image analysis apparatus

The invention claimed is:

1. An image analysis apparatus for analyzing orientations of fiber bundles of X-yarns and Y-yarns from a three-dimensional image of a woven fabric made of fiber bundles of the X-yarns, the Y-yarns, and Z-yarns,
the image analysis apparatus comprising:
a binarization unit that binarizes the three-dimensional image;
an overlapping area extraction unit that extracts an overlapping area, in which the X-yarns and the Y-yarns perpendicularly and three-dimensionally intersect with each other, from the binarized image;
a reference direction determination unit that averages an overlapping direction of each voxel included in the overlapping area and determines the averaged direction as a reference direction;
a Z-yarn removal unit that removes the Z-yarns from the binarized image by applying a directional distance method on a reference plane perpendicular to the reference direction; and
a fiber bundle orientation estimation unit that applies the directional distance method again to the image, from which the Z-yarns have been removed, on the reference plane and estimates the orientations of the fiber bundles of the X-yarns and the Y-yarns on the basis of a directional distance calculated upon the application.

2. The image analysis apparatus according to claim 1, wherein the binarization unit:
binarizes the three-dimensional image on the basis of a specified threshold value; and
executes closing processing on the image after the binarization.

3. The image analysis apparatus according to claim 2, wherein the overlapping area extraction unit:
executes opening processing on the image after the closing processing;
executes dilation processing on the image after the opening processing; and
extracts the overlapping area by calculating a product set of the image after the dilation processing and the image after the closing processing.

4. The image analysis apparatus according to claim 1, wherein the reference direction determination unit:
applies the directional distance method to the overlapping area and estimates the overlapping direction of each voxel included in the overlapping area on the basis of the directional distance of each voxel calculated upon the application;
extracts a central area by executing erosion processing on the overlapping area; and
averages the overlapping direction of each voxel included in the central area and determines the averaged direction as the reference direction.

5. The image analysis apparatus according to claim 1, wherein the Z-yarn removal unit:
applies the directional distance method on the reference plane and calculates an eigenvector for a second largest eigen value of a directional tensor on the basis of the directional distance of each voxel which is calculated upon the application;
separates the binarized image into an area of the X-yarns or the Y-yarns and an area of the Z-yarns on the basis of the eigenvector; and
removes the Z-yarns from the binarized image by removing voxels included in the Z-yarns area.

6. The image analysis apparatus according to claim 5, wherein upon calculating a directional distance of a voxel of interest, the Z-yarn removal unit proceeds with voxels in a direction indicated by an eigenvector of the voxel of interest and a direction opposite to the direction indicated by the eigenvector; and when the Z-yarn removal unit reaches a background or an angle formed with a direction indicated by an eigenvector of a next voxel to proceed is larger than a specified threshold value, the Z-yarn removal unit stops proceeding and calculates a distance between respective last reached voxels as a conditional directional distance; and
the Z-yarn removal unit separates the binarized image into the area of the X-yarns or the Y-yarns and the area of the Z-yarns on the basis of the conditional directional distance.

7. The image analysis apparatus according to claim 1, wherein the Z-yarn removal unit:
executes dilation processing after removing the Z-yarns from the binarized image; and
calculates a product set of the image after the dilation processing and the image before the dilation processing.

8. The image analysis apparatus according to claim 1, wherein the fiber bundle orientation estimation unit:
applies the directional distance method again to the image, from which the Z-yarns have been removed, on the reference plane and estimates the orientations of the fiber bundles of the X-yarns and the Y-yarns;
extracts voxels in a vicinity of a central part from among the voxels for which the orientations of the fiber bundles are estimated;
executes clustering processing on the voxels in the vicinity of the central part; and
eliminates noise by deleting a cluster in which a minimum voxel belongs.

9. The image analysis apparatus according to claim 1, comprising a display unit that displays an image showing the orientations of the fiber bundles of the X-yarns and the Y-yarns.

10. An image analysis method for analyzing orientations of fiber bundles of X-yarns and Y-yarns from a three-dimensional image of a woven fabric made of fiber bundles of the X-yarns, the Y-yarns, and Z-yarns, the image analysis method comprising the following steps executed by a computer:

a first step of binarizing the three-dimensional image;

a second step of extracting an overlapping area, in which the X-yarns and the Y-yarns perpendicularly and three-dimensionally intersect with each other, from the binarized image;

a third step of averaging an overlapping direction of each voxel included in the overlapping area and dete lining the averaged direction as a reference direction;

a fourth step of removing the Z-yarns from the binarized image by applying a directional distance method on a reference plane perpendicular to the reference direction; and a fifth step of applying the directional distance method again to the image, from which the Z-yarns have been removed, on the reference plane and estimating the orientations of the fiber bundles of the X-yarns and the Y-yarns on the basis of a directional distance calculated upon the application.

11. A non-transitory computer readable storage medium storing a computer program for analyzing orientations of fiber bundles of X-yarns and Y-yarns from a three-dimensional image of a woven fabric made of fiber bundles of the X-yarns, the Y-yarns, and Z-yarns, the program causing a computer to execute:

a first step of binarizing the three-dimensional image;

a second step of extracting an overlapping area, in which the X-yarns and the Y-yarns perpendicularly and three-dimensionally intersect with each other, from the binarized image;

a third step of averaging an overlapping direction of each voxel included in the overlapping area and determining the averaged direction as a reference direction;

a fourth step of removing the Z-yarns from the binarized image by applying a directional distance method on a reference plane perpendicular to the reference direction; and a fifth step of applying the directional distance method again to the image, from which the Z-yarns have been removed, on the reference plane and estimating the orientations of the fiber bundles of the X-yarns and the Y-yarns on the basis of a directional distance calculated upon the application.

12. An image analysis apparatus comprising:

a binarization unit that binarizes a three-dimensional image of a woven fabric made of fiber bundles of X-yarns, Y-yarns, and Z-yarns;

an overlapping area extraction unit that extracts an overlapping area, in which the X-yarns and the Y-yarns perpendicularly and three-dimensionally intersect with each other, from the binarized image; and an overlapping area morphological analysis unit that analyzes a form of the extracted overlapping area.

13. The image analysis apparatus according to claim 12, wherein the overlapping area morphological analysis unit further detects an abnormal orientation of the fiber bundles of the X-yarns or the Y-yarns on the basis of a result of the analysis of the form of the overlapping area.

14. The image analysis apparatus according to claim 12, wherein the overlapping area morphological analysis unit calculates a volume of the overlapping area.

15. The image analysis apparatus according to claim 12, wherein the overlapping area morphological analysis unit calculates an extending direction of the overlapping area.

16. The image analysis apparatus according to claim 12, wherein the overlapping area morphological analysis unit calculates a centroid position of a plurality of overlapping areas.

* * * * *